(12) United States Patent
Matsumoto

(10) Patent No.: US 8,617,540 B2
(45) Date of Patent: Dec. 31, 2013

(54) COMBINATIONAL CHEMOTHERAPY TREATMENT

(75) Inventor: Yoshihiro Matsumoto, Melrose Park, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 547 days.

(21) Appl. No.: 12/760,673

(22) Filed: Apr. 15, 2010

(65) Prior Publication Data

US 2010/0266565 A1  Oct. 21, 2010

Related U.S. Application Data

(60) Provisional application No. 61/169,526, filed on Apr. 15, 2009.

(51) Int. Cl.
*A61K 38/43* (2006.01)
*A61K 31/7068* (2006.01)
*A61P 35/00* (2006.01)

(52) U.S. Cl.
USPC ....................................... 424/94.1

(58) Field of Classification Search
USPC ....................................... 424/94.1
See application file for complete search history.

(56) References Cited

U.S. PATENT DOCUMENTS

| | | | |
|---|---|---|---|
| 5,496,810 A * | 3/1996 | Schwartz | 514/50 |
| 6,344,447 B2 * | 2/2002 | von Borstel et al. | 514/49 |
| 2008/0050425 A1 * | 2/2008 | Lewis et al. | 424/450 |

OTHER PUBLICATIONS

Prietzsch et al., "Interferon-alpha inhibits cell cycle progression by Ba/F3 cells through the antagonisation of interleukin-3 effects on key regulators of G1/S transition" Cellular Signaling , 14:751-759, 2002.*
Boorstein, Effect of Hydroxymethyluracil and 3-Aminobenzamide on the repair and toxicity of 5-hydroxymethyl-2'-deoxyuridine in Mammalian Cell, Cancer Research, 49:1509-1514, 1989.*
Waschke et al., 5-Hydroxymethyl-2'-deoxyuridine, a normal DNA constituent in certain Bacillus subtilis phages is cytostatic for mammalian cells, Nature, 255(5510):629-630, 1975.*
O'Connor, Owen A., "Pharmacological Modulation of Fluoropyrimidines—Building on the Lessons of the Paast", Cancer Drug Discovery and Development: CombinationCancer Therapy: Modulators and Potentiators, ed. Humana Press Inc., Totowa, NJ pp. 133-174.
O'Connor, O.A., et al. "Pharmacological Modulation of Fluoropyrimidines: Building on the lessons of the past." In: Combination Cancer Therapy: Modulators and Potentiators (Schwartz, G.K., ed.). pp. 133-174. Humana Press Inc., Totowa, NJ, 2005.
Waschke, S., et al. "5-hydroxymethyl-2'-deoxyuridine, a normal DNA constituent in certain *Bacillus subtilis* phages is cytostatic for mammalian cells." Nature. Jun. 19, 1975;255(5510):629-30.
Kahilainen, L., et al. "In vitro and in vivo studies of a promising antileukemic thymidine analogue, 5-hydroxymethyl-2' deoxyuridine." Biochem Pharmacol. Dec. 1, 1986;35(23):4211-5.
Vilpo, J.A., et al. "Antileukemic activity against L1210 leukemia, pharmacokinetics and hematological side effects of 5-hydroxymethyl-2'-deoxyuridine." Leuk Res. 1987;11(10):877-80.
"Cell Proliferation Reagent WST-1." Roche Applied Science, US Online Product Catalog, Package Inserts/Product Instructions. https://www.roche-applied-science.com/pack-insert/1644807a.pdf. Accessed Apr. 19, 2010.
Dreβler, V., et al. "CombiTool—A New Computer Program for Analyzing Combination Experiments with Biologically Active Agents." Comp. Biomed. Res. Apr. 1999;32(2):145-161.
Saiko, P., et al. "Heterodinucleoside phosphates of 5-fluorodeoxyuridine and arabinofuranosylcytosine—new drugs in cancer chemotherapy?" In Vivo. Jan.-Feb. 2005;19(1):205-14.

* cited by examiner

*Primary Examiner* — Jeffrey S. Lundgren
*Assistant Examiner* — Zenab Olabowale
(74) *Attorney, Agent, or Firm* — Dann, Dorfman, Herrell & Skillman; Kathleen D. Rigaut

(57) ABSTRACT

Disclosed is a composition comprising a therapeutically effective amount of (a) at least one compound from the group of 5-fluorouracil, 5-fluorodeoxyuridine, capecitabine or a prodrug of such compounds; and (b) 5-hydroxymethyl-2'-deoxyuridine, or a prodrug of such compound, as well as kits comprising such composition and methods of use thereof for treating neoplasia.

13 Claims, 28 Drawing Sheets

Effect of 5-FU and HmdUrd on HT29 Growth

Effect of 5-FU and HmdUrd on HCT116 Growth

Effect of 5-FU and HmdUrd on Panc-1 Growth

Effect of 5-FU and HmdUrd on EKVX Growth

Effect of 5-FU and HmdUrd on MDA-MB-231 Growth

Effect of 5-FU and HmdUrd on SID-507 Growth (7 days)

A

B

Effect of 5-FU and HmdUrd on SID-509 Growth (7 days)

Effect of 5-FU and HmdU on W-38 Growth

Effect of 5-FU and HmU (Cayman) on HT29 Growth

Effect of 5-FU and HmU (Aldrich) on HT29 Growth

Effect of 5-FU and dUrd on HT29 Growth

Effect of 5-FU and OHdU on HT29 Growth

Effect of deoxyadenosine and HmdUrd on HT29 Growth

Effect of Raltitrexed and HmdUrd on HT29 Growth

Clonogenic assay of HT-29 cells treated with 0.5 µM FU and 5 µM HmdU indicates that the combined treatment causes irreversible cell death.

A Time course.

B Synergy of combined drugs. Drug treatment for 48 hours.

A  Cell cycle analysis of synchronized HT-29 cells

B  Effect of 3-aminobenzamide and caffeine on HT-29 cell cycle.

Effect of the SMUG1 knockdown and overexpression on sensitivity to 5-FU and HmdU A Relative quantity of SMUG1 mRNA B Immunoblot detection of SMUG1 protein Effect of the SMUG1 knockdown and overexpression
on sensitivity to 5-FU and HmdU C  Normal HT29 cell line D  SMUG1-kockdown cell line Effect of the SMUG1 knockdown and overexpression on sensitivity to 5-FU and HmdU E  SMUG1-overexpression cell line #6

F  SMUG1-overexpression cell line #9

Incorporation of 5-FU and HmdU into DNA or RNA

A

5-FU incorporation into DNA after 24 h

B

HmdU inconrporation into DNA after 24 h

Incorporation of 5-FU and HmdU into DNA or RNA

C

D

Treatment with 5-FU and HmdUrd does not induce PARP1 cleavage in HT29.

Effect of PARP1 inhibitors on HT29 with 5-FU and HmdU

A  Effect of 3-aminobenzamide (3AB)

B  Effect of 4-amino-1,8-naphtalimide (4AN)

Comet assay for detection of single-strand breaks and/or alkali labile sites generated by 5-FU/HmdU treatment A Synergistic effect of 5-FU and HmdU on ssb/als formation B Time course of ssb/als formation by 5-FU/HmdU treatment

COMBINATIONAL CHEMOTHERAPY TREATMENT

This application claims priority under 35 U.S.C. §119(e) to U.S. Provisional Patent Application 61/169,526, filed on Apr. 15, 2009. The entire foregoing application is incorporated by reference herein.

FIELD OF THE INVENTION

This invention relates to the field of medicine and the treatment of cancer. More specifically, the present invention provides improved combinational chemotherapeutic regimens.

BACKGROUND OF THE INVENTION

Several publications and patent documents are cited throughout this application in order to more fully describe the state of the art to which this invention pertains. The disclosure of each of these citations is incorporated by reference herein.

The National Cancer Institute has estimated that in the United States one out of three people will be afflicted with cancer during their lifetime. Furthermore, over 50% of those contracting cancer will eventually succumb to the disease. The widespread occurrence of the disease underscores the need for improved anticancer regimens for the treatment of neoplasia and malignancy.

Due to the wide variety of cancers presently observed, numerous anticancer agents and treatment modalities have been developed to inhibit cancer growth within the body. These agents are administered to patients with the objective of destroying or otherwise preventing the growth of neoplastic cells.

One such chemical compound is 5-Fluorouracil (5-FU) which is a pyrimidine analog in the family of antimetabolite drugs which is incorporated into DNA and inhibits thymidylate synthase (TS). Another potential approach involves harnessing the cytotoxic effects of nucleoside/base analogs, such as the oxidized DNA base, 5-hydroxymethyl-2'-deoxyuridine ("HmdU" or "HmdUrd").

In order to treat the large number of cancer patients, other avenues, such as new combinations of known agents need to be developed. However, these efforts are hampered by the lack of knowledge of which combinations are effective and which combinations may provide synergistic results.

SUMMARY OF THE INVENTION

In accordance with the present invention, methods of treating neoplasia are provided. An exemplary method entails administering to a patient a therapeutically effective amount of at least one of the compounds selected from the group consisting of 5-Fluorouracil, 5-Fluorodeoxyuridine, and capecitabine, in combination with 5-hydroxymethyl-2'-deoxyuridine or prodrugs thereof. In another aspect of the invention, the compounds are administered simultaneously. In other aspects, the compounds are administered sequentially. Preferred embodiments of the methods are useful for treating solid and liquid tumors.

In another embodiment of the invention compositions are provided comprising at least one of the compounds selected from the group consisting of 5-Fluorouracil, 5-Fluorodeoxyuridine, and capecitabine; 5-hydroxymethyl-2-deoxyuridine and prodrugs thereof and a pharmaceutically acceptable carrier. In an alternative embodiment, heterodinucleoside phosphates consisting of 5-Fluorodeoxyuridine and 5-hydroxymethyl-2'-deoxyuridine are provided.

In yet another embodiment, kits are provided for the treatment of neoplasia comprising the synergistic combinations of antineoplastic compounds disclosed herein. In another aspect, the kits further comprise buffers, containers, and instructional materials.

BRIEF DESCRIPTION OF THE FIGURES

FIG. 7 panels A and B used HmU provided by Cayman, and FIG. 7 panels C and D used HmU provided by Aldrich.

DETAILED DESCRIPTION OF THE INVENTION

Figure 1:
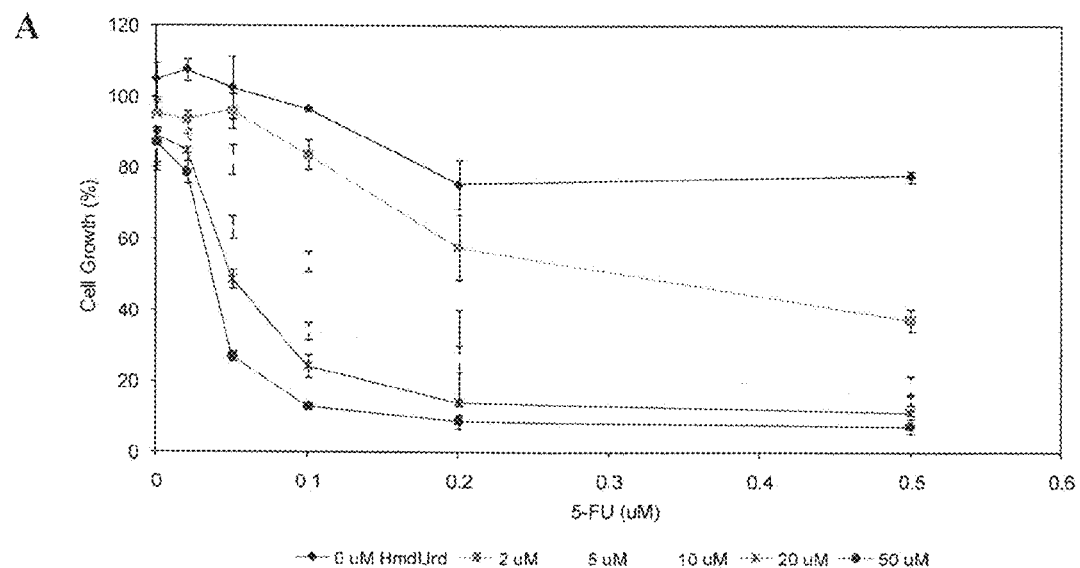
FIG. 1 shows the effect of combined 5-FU and HmdU treatment on the growth of HT-29 cells (FIG. 1 panels A-B) and HCT116 cells (FIG. 1 panels C-D).
Figure 1:
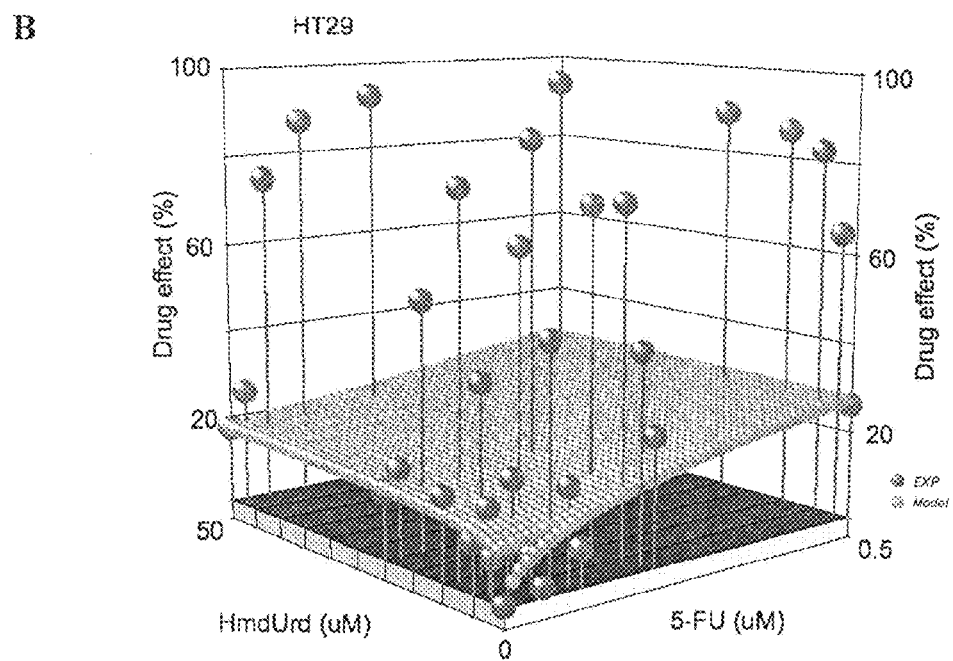
Figure 1:
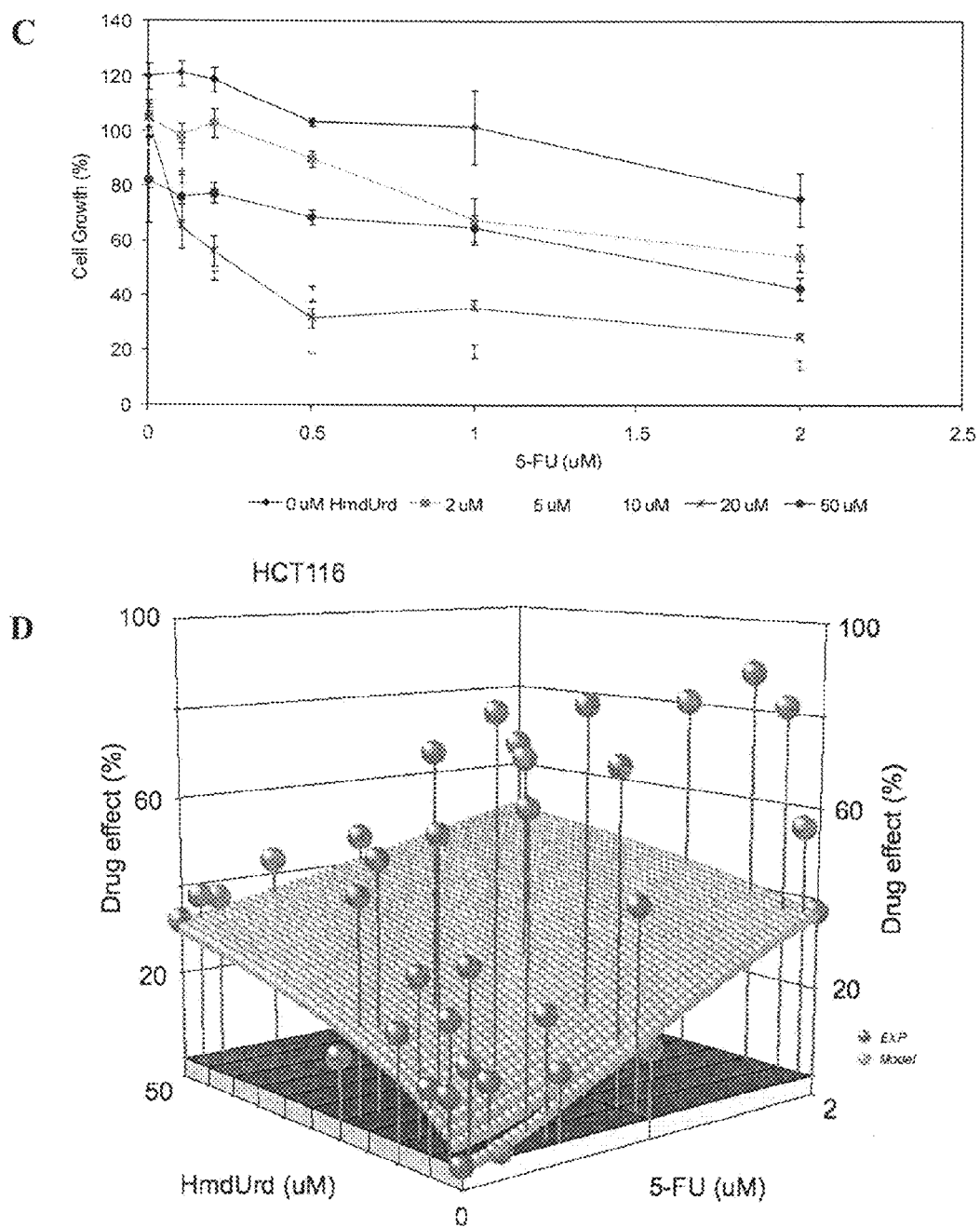

The present inventor has discovered that 5-FU and its derivatives can act synergistically when used in combination with certain nucleoside base analogs. The arrangement of certain embodiments of the instant invention is based, at least in part, on the finding that certain combinations of chemotherapeutic agents are preferentially associated with synergistic cytotoxic effects on cancer cells. Accordingly, chemotherapeutic and antineoplastic agents can be preferentially combined. The arrangements of certain embodiments of the invention also pertain to methods useful in treating or preventing conditions that would benefit from cytotoxic effects on proliferating cells.

In a particular embodiment, the methods comprise administration of the antimetabolite having the following structure I:

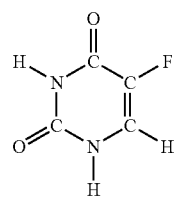

(I)

used in combination with a base analog compound having the structure II:

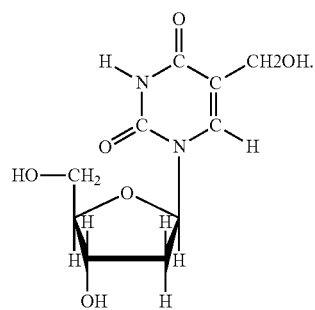

(II)

In another embodiment of the invention, pharmaceutically acceptable salts of Structures I and II can be administered to a patient. Prodrugs of Structure I and II and derivatives thereof are also contemplated as being part of this invention.

Embodiments of the invention provide methods for the synergistic treatment of a variety of cancers, including, but not limited to: carcinomas, including that of the bladder (including accelerated and metastatic bladder cancer), breast, colon, kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); and hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma.

In a preferred embodiment of the invention, a method is provided for the synergistic treatment of colon, pancreatic and lung tumors. Advantageously, the synergistic method of this invention reduces the development of tumors, reduces tumor burden, or produces tumor regression in a mammalian host.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference.

The present invention also encompasses a pharmaceutical composition useful in the treatment of cancer, comprising a therapeutically effective amount of the combination of antineoplastic, chemotherapeutic agents of Structure I and Structure II, or derivatives and prodrugs thereof (e.g., for Structure (I) 5-Fluorodeoxyuridine and capecitabine, and for Structure (II) prodrugs resulting from the modification of 5-hydroxymethyl-2'-deoxyuridine), with or without pharmaceutically acceptable carriers or diluents. The methods of the invention entail the use of antineoplastic agents in combination of Structure I and/or Structure II. Certain arrangements of particular embodiments of the invention also include the use of derivatives of the antineoplastic chemotherapeutic agents of Structure I and/or Structure II. Chemotherapeutic treatment modalities and anticancer compounds for the treatment of cancers also include a group of heterodinucleoside phosphates (i.e., dimers) consisting of two compounds, 5-Fluorodeoxyuridine and 5-hydroxymethyl-2'-deoxyuridine, which offer additional treatment paradigms as reviewed in Saiko et al. (In vivo (2005) 19:205-214).

The compositions of the present invention may further comprise one or more pharmaceutically acceptable additional ingredient(s), such as alum, stabilizers, antimicrobial agents, buffers, coloring agents, flavoring agents, adjuvants, and the like. In a particular embodiment, the compositions of the instant invention comprise 5-FU, HmdU, and at least on pharmaceutically acceptable carrier.

One skilled in the art appreciates that a pharmaceutical composition comprising a combination of Structure I and Structure II or derivatives thereof can be administered to a subject by various routes including, for example, injection directly into a tumor, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. In a particular embodiment, the drugs are administered parenterally as a solution in normal saline.

The skilled artisan may administer the combination of 5-FU and HmdU alone, or in combination, with at least one more chemotherapeutic agent or therapy, based on the clinical signs and symptoms exhibited by the individual and would monitor the effectiveness of such treatment using routine methods such as radiologic, immunologic, or where indicated, histopathologic methods. Certain cancers can be treated effectively with compounds of Structure I and Structure II and a plurality of anticancer agents. Such agents can include microtubule-stabilizing agents, microtubule-disruptor agents, alkylating agents, anti-metabolites, epidophyllotoxins, antineoplastic enzymes, topoisomerase inhibitors, inhibitors of cell cycle progression, and platinum coordination complexes. Such multiple combinations can provide greater efficacy and are within the scope of the invention. In a preferred embodiment of the invention a combination of Structure I and II are administered in conjunction. Optionally, as mentioned above, the aforementioned compounds are administered with at least one antineoplastic agent. The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

When 5-FU and HmdU are administered in combination with at least one other agent, all the agents can be co-administered in the same formulation. Alternatively, the various agents can be administered simultaneously in separate formulations. In addition, the agents can be administered in separate formulations, where the separate formulations are not administered simultaneously but are administered during the same period of treatment, for example, during a daily or weekly period of treatment.

The combinations of the present invention may also be used in conjunction with other well known therapies that are selected for their particular usefulness against the condition that is being treated. It is also understood that the instant combination of antineoplastic agent(s) and Structure I and Structure II compounds may be used in conjunction with other methods of treating cancer (preferably cancerous tumors) including, but not limited to, radiation therapy and surgery.

Administration of the pharmaceutical preparation is preferably in a "therapeutically effective amount," this being sufficient to show benefit to the individual. This amount prevents, alleviates, abates, or otherwise reduces the severity of symptom associated with neoplasia in a patient. As used herein the therapeutically effective amount is a therapeutically "synergistic" effective amount, with "synergistic" referring to an amount which results in a more than additive effect of each component used alone.

If formulated as a fixed dose, the active ingredients of the combination compositions of this invention are employed within predefined dosage ranges. For example, the 5-FU compound can be administered to humans at a dose in the range of 1-150 mg/kg/day, 5-75 mg/kg/day, or 10-50 mg/kg/day; not to exceed 800 mg/day. HmdU can be administered at a ratio compared to 5-FU administration that produces synergistic cytotoxicity; for example, at a ratio of 1:2 (5-FU:HmdU), 1:3, 1:4, 1:5, or a ratio of 1:6 or greater, such as 1:10, 1:20, 1:30, 1:40, 1:50 or greater. In a particular embodiment, the ratio is 1:20 (5-FU:HmdU).

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

A pharmaceutical preparation of the antineoplastic agents is formulated in dosage unit form for ease of administration and uniformity of dosage. Dosage unit form, as used herein, refers to a physically discrete unit of the antineoplastic agents appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

As described hereinbelow, the invention has been tested in vitro using cultured cell line. The combination treatment may also be tested through in vivo animal model experiments and subsequent clinical trials.

For purposes of the present invention, a "neoplasm" or "neoplasia" means a proliferative disease characterized by the abnormal proliferation of cells. Typically, neoplasia is associated with cancer and tumor formation. As used herein a "solid tumor" is one that occurs in an organ, such as the breast or the lung, and a "liquid tumor" consists of blood cells that have become cancerous, such as leukemia.

As used herein the term "administering" or "administration" as used herein means the introduction of a foreign molecule into a cell or host. The term is intended to be synonymous with the term "delivery". Suitable routes of administration, without limitation, are intravenous, intra-arterial, intramuscular, subcutaneous, intrasynovial, infusion, sublingual, transdermal, oral, or topical.

The term "treating" or the phrase "to treat" as used herein refers to any type of treatment that imparts a benefit to a patient afflicted with a disease, including improvement in the condition of the patient (e.g., in one or more symptoms), delay in the progression of the condition, etc.

The term "patient" refers to an individual afflicted with a disease characterized by neoplasia. In particular, a patient (i.e., a host) is an animal (i.e., mammal) or human. In a particularly preferred embodiment, a patient refers to a human.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity and "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

The term "therapeutically effective amount" is the amount present that is delivered to a subject to provide the desired physiological response. Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al.

As used herein, the phrase "antineoplastic agent" is synonymous with "chemotherapeutic agent" and "antiproliferative agent" and refers to compounds that prevent cancer, or hyperproliferative cells from multiplying. Generally, antineoplastic agents may prevent cancer cells from multiplying by: (1) interfering with the cell's ability to replicate DNA and (2) inducing cell death and/or apoptosis in the cancer cells.

As used herein, a "combination," "combinational" or "combined" treatment refers to the use of 5-FU or derivatives thereof in conjunction with HmdU or derivatives thereof.

The term "derivatives" as used herein refer to compounds or agents that are structurally or functionally related to the compounds shown in Structure I or Structure II, respectively (i.e., 5-Fluorodeoxyuridine and capecitabine). It is understood that derivatives of the Structure I and II compounds can be substituted in the methods of the instant invention for synergistic cytotoxicity of proliferating cells.

As used herein, "prodrug" means compounds that are drug precursors which, following administration to a subject, release the drug in vivo via some chemical or physiological process (e.g., a prodrug on being brought to the physiological pH or through enzyme action is converted to the desired active drug form. The prodrug can be converted into a product that is toxic to tumor cells.

The phrase "synergistic cytotoxic effects" refers to the use of at least two compounds to provide greater cytotoxic effects than the combined additive effects of the compounds when used individually.

Methods of Treatment

The antineoplastic compounds of the instant invention may be used in combination. A particularly preferred combination comprises 5-FU and HmdU. Combinations of derivatives of 5-U and HmdU are also encompassed in certain arrangements of the invention. For example, at least one compound that is functionally or structurally related to HmdU may be used in combination with 5-FU. Similarly, at least one 5-FU functionally or structurally related compound, for example, 5-Fluorodeoxyuridine (5-FdU) or capecitabine can be used in combination with HmdU. As mentioned previously, the combinational chemotherapy can be administered with at least one other agent.

Kits

In another embodiment of the invention, kits are provided for practicing the methods of the instant invention. The kits encompassed by the invention are useful for treating neoplasia. Such kits may comprise compositions of Structure I and II, or derivatives thereof, and optionally at least one other antineoplastic agent. The kit may further comprise buffers, and other compositions to aid in administration to a host in need of treatment. The compositions may be formulated for specific dosing regimens. Each composition or solution may be contained in a vial or bottle and all components included in a box for commercial sale. The pharmaceutical compositions can be included in a container, pack, or dispensed together with instructional materials. The kits may comprise a single composition comprising both Structure I and Structure II, or comprise separate compositions of Structure I and Structure II.

The following materials and methods are provided to facilitate practice of the present invention:

Analysis of Combination Experiments with Biologically Active Agents

Cell Growth Assays

In a typical cell growth assay, cells were plated in 96-well plates on Day 0, and indicated concentrations of drugs were added on Day 1. Each condition was replicated in triplicate. Subsequently, quantities of metabolically active cells in each well were measured by WST-1 assay on Day 4. The WST-1 assay (assay reagents from Roche) measures the concentration of formazan converted from a tetrazolium salt, WST-1, by a mitochondrial succinate-tetrazolium-reductase system.

CombiTool

CombiTool is a computer program for the analysis of combination effects of biologically active agents and is described in Dressler et al. (Computers and Biomedical Research (1999) 32:145-160). It performs model calculations and an analysis of experimental combination effects for two or three agents according to both the Bliss independence and the Loewe additivity criteria. Zero interaction response surfaces are calculated from single-agent dose-response relations and compared to experimental combination data. The calculation of response surfaces for Loewe additivity is based on a new approach which combines the implicit definition equation in terms of doses alone with single-agent dose-response relations. CombiTool has a built-in graphics facility which allows for the direct visualization of the response surfaces or the corresponding contour plots and the experimental data.

Animal Studies on Toxicity

Chemicals

HmdU ($C_{10}H_{14}N_2O_6$, MW and FW=258.23, 95% pure) and 5-FU ($C_4H_3FN_2O_2$, MW and FW=130.08, 99% pure) were stored as white powder, protected from light at 4° C. To prepare each compound for administration, each compound was weighed out for all five treatments. The dosing solutions were prepared at twice (2×) the concentration needed for the study so that when mixed at a 1:1 (v/v) ratio for each day of treatment the 2× stocks were diluted to the final dose concentration necessary. HmdU was dissolved in 1×PBS and then briefly vortexed to prepare the 2× stock. The resulting solution was clear and colorless with a pH value of 7.11. 5-FU was dissolved in 1×PBS and sonicated for ~2-3 minutes to prepare the 2× stock. The resulting solution was clear and colorless with a pH value of 6.87. Lower dosage levels were prepared by direct dilution of the top dose with 1×PBS. The separate 2× solutions (for each dosage level) were prepared prior to the start of treatment, combined at a ratio of 1:1 (v/v), aliquoted out for each daily dose, and stored frozen at −20° C. until use. On each treatment day one aliquot of each dosage level was thawed at room temperature and dosed per protocol. Any solution remaining after the daily dose was discarded.

Mice

Female mice (Crl:NU-Foxn1nu) were obtained from Charles River Laboratories. They were 9-10 weeks old on Day 1 of the experiment. The mice were fed irradiated Rodent Diet 5053 (LabDiet™) and water ad libitum. Mice were housed in static cages with Bed-O'Cobs™ bedding inside Biobubble® Clean Rooms that provide H.E.P.A filtered air into the bubble environment at 100 complete air changes per hour. All treatments and body weight determinations were carried out in the bubble environment. The environment was controlled to a temperature range of 70°±2° F. and a humidity range of 30-70%.

All mice were observed for clinical signs at least once daily. Mice found in obvious distress or in a moribund condition were euthanized. All procedures carried out in this experiment were conducted in compliance with all the laws, regulations and guidelines of the National Institutes of Health (NIH).

Treatments

Treatments began on Day 1. All mice weighed≥21.3 g at the initiation of therapy. Mean group body weights at first treatment were well-matched (range of group means, 21.7-25.4 g). All mice were dosed according to individual body weight on the day of treatment (0.2 ml/20 g) as indicated. Primary endpoints for this study were mortality, weight loss, clinical signs and necropsy observations.

Assessment of Side Effects

All mice were observed for clinical signs at least once daily. Individual body weights were recorded thrice weekly. Treatment-related weight loss in excess of 20% is generally considered unacceptably toxic. A dosage level is described as tolerated if treatment-related weight loss (during and two weeks after treatment) is <20% and mortality is ≤10%. Upon death or euthanasia, all mice were necropsied to provide a general assessment of potential cause of death and perhaps target organs for toxicity.

The following examples illustrate certain embodiments of the invention. They are not intended to limit its scope in any way.

Example I

Response of Various Cell Lines to Combination Treatment with 5-FU and HmdU

Figure 2:
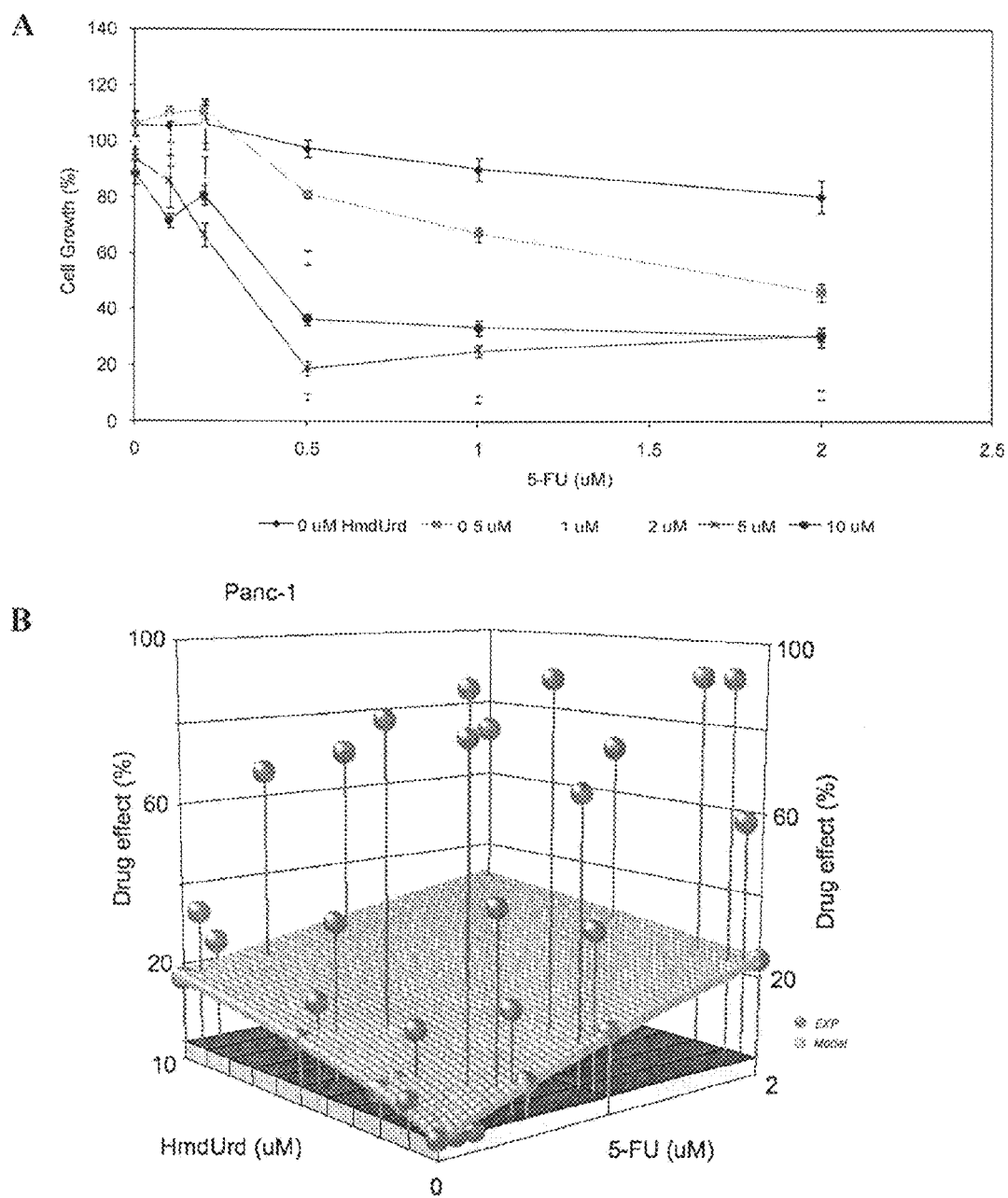
FIGS. 2A and B show the effect of combined 5-FU and HmdU treatment on Panc-1 cell growth.
Figure 3:
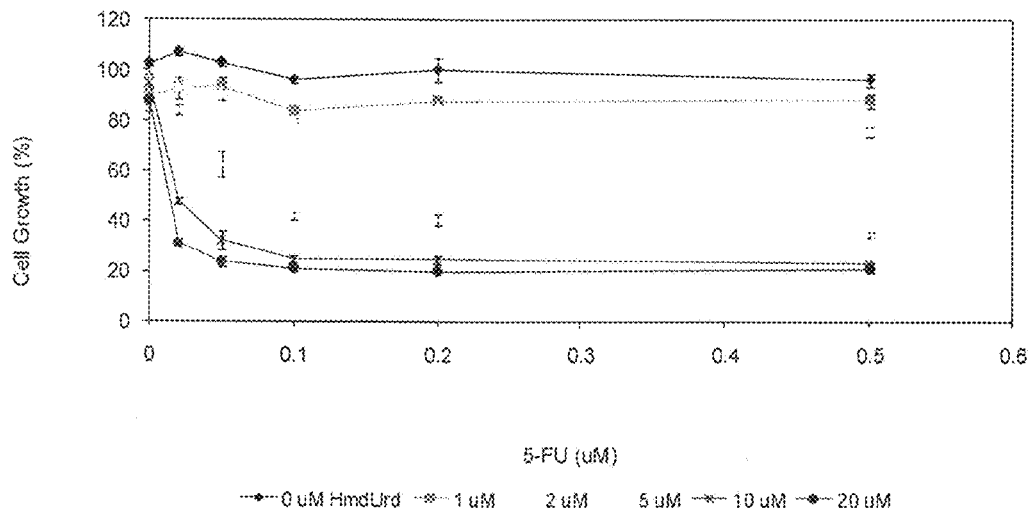
FIGS. 3A and B show the effect of combined 5-FU and HmdU treatment on EKVX cell growth.
Figure 3:
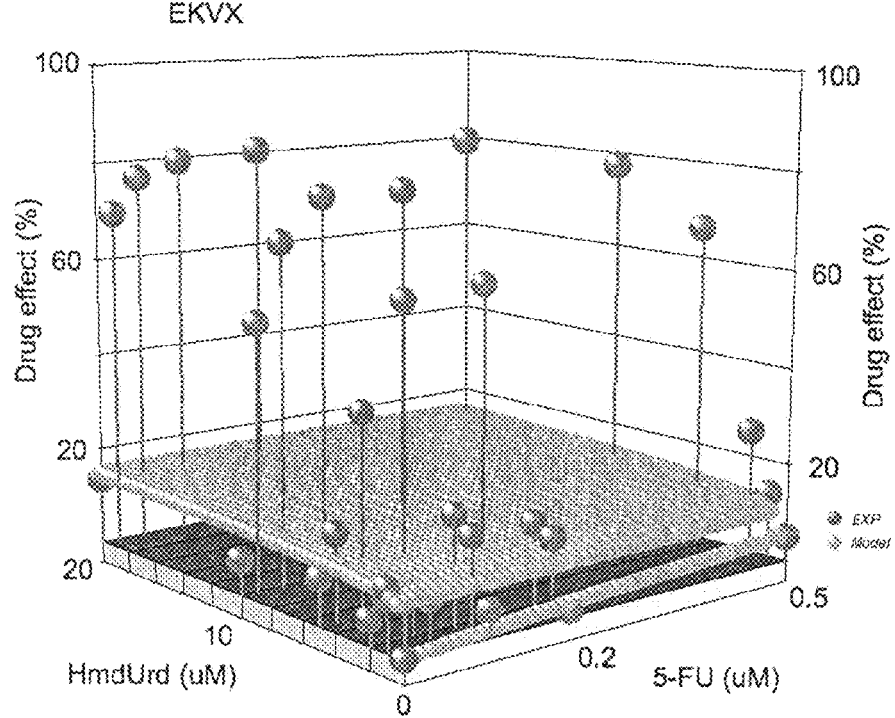

In the present example, the in vitro effects of 5-FU and HmdU treatment were assessed in several cell lines. FIG. 1A shows the effect of a combined 5-FU and HmdU (i.e., HmdUrd) treatment regime on HT-29 colon cancer cells. FIG. 1B show the results interpreted with the CombiTool program which indicates synergistic experimental data by large gray circles above the lower additive results when the drugs are used alone. Overall, FIG. 1B demonstrates increased sensitivity to these drugs when administered in combination. FIGS. 1C and 1D show similar results from experiments in the colon cancel cell line, HCT116. As indicated by the results, 5-FU and HmdU demonstrate synergistic cytotoxicity to the cells. Likewise, the combined effects of treatment with 5-FU and HmdU indicates synergy as shown in FIGS. 2A and 2B when administered to the panc-1, pancreatic cancer cell line. The results of the same combination treatment on the lung cancer cell line EKVX appears in FIGS. 3A and B and the combination also has enhanced cytotoxic effects when administered to the cells. These increased cytotoxic effects of the combination therapy in the cell lines of FIGS. 1-3 is more than 80% with 0.5 uM 5-FU and 10 uM HmdU which indicated that the treatment is not additive. Furthermore, the combination index of the inhibition of HT-29 cells was less than 0.1 for 50% inhibition, which indicates strong synergy when the two compounds are used in combination.

Figure 4:
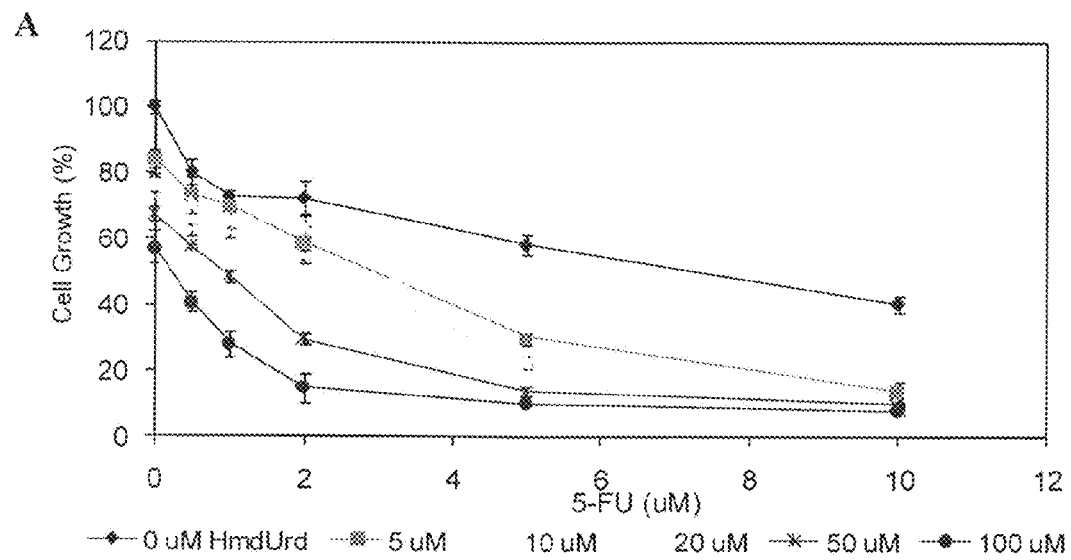
FIGS. 4A and B show the effect of combined 5-FU and HmdU treatment on MDA-MB231 cell growth.
Figure 4:
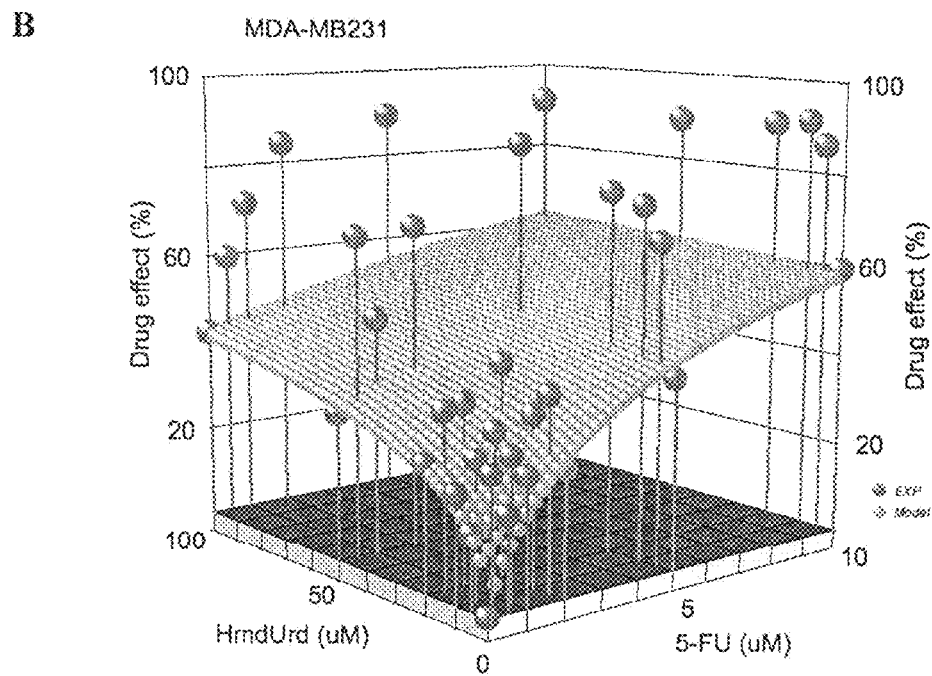
Figure 5:
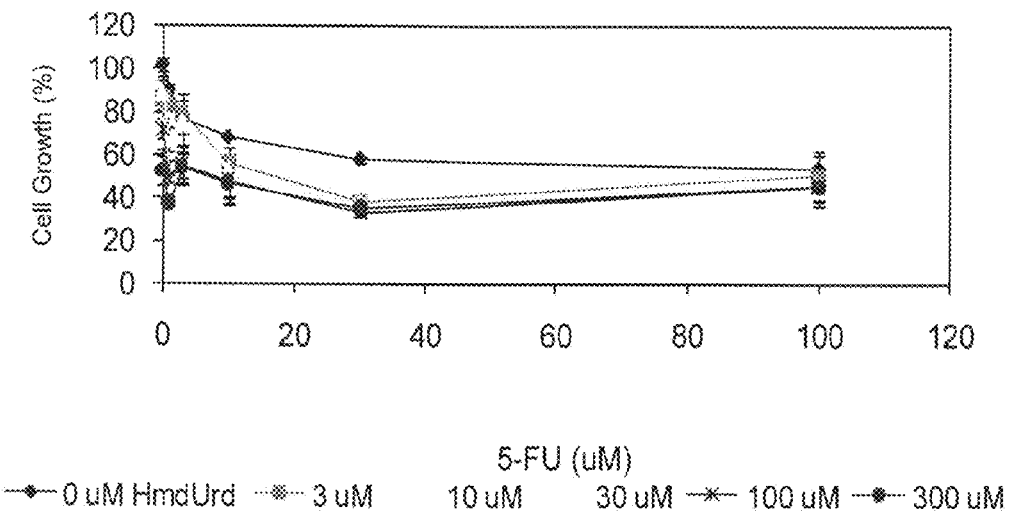
FIG. 5 shows the effect of combined 5-FU and HmdU treatment on SID-507 (FIG. 5 panels A and B) and SID-509 (FIG. 5 panels C and D) cell growth.
Figure 5:
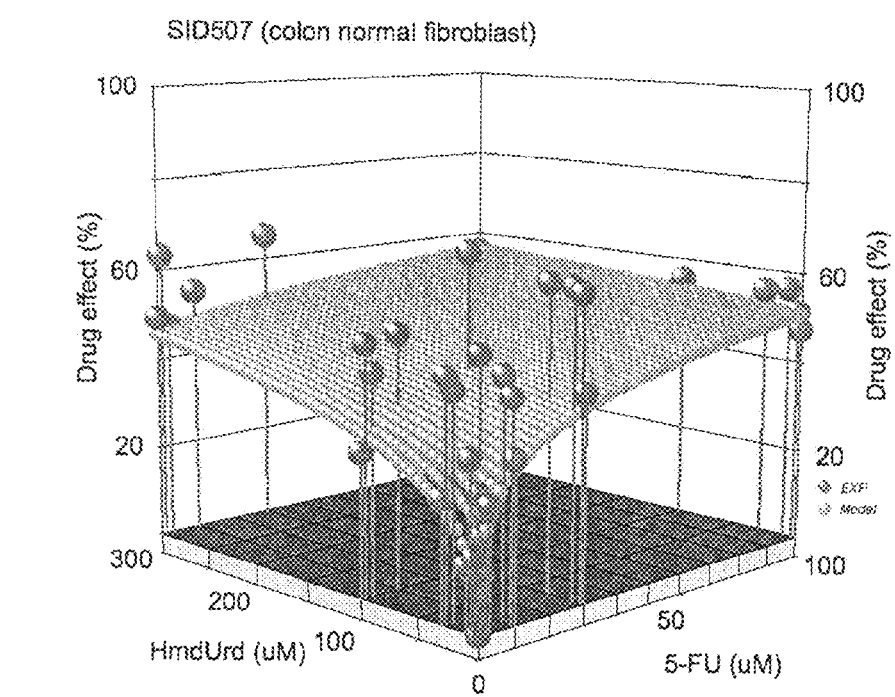
Figure 5:
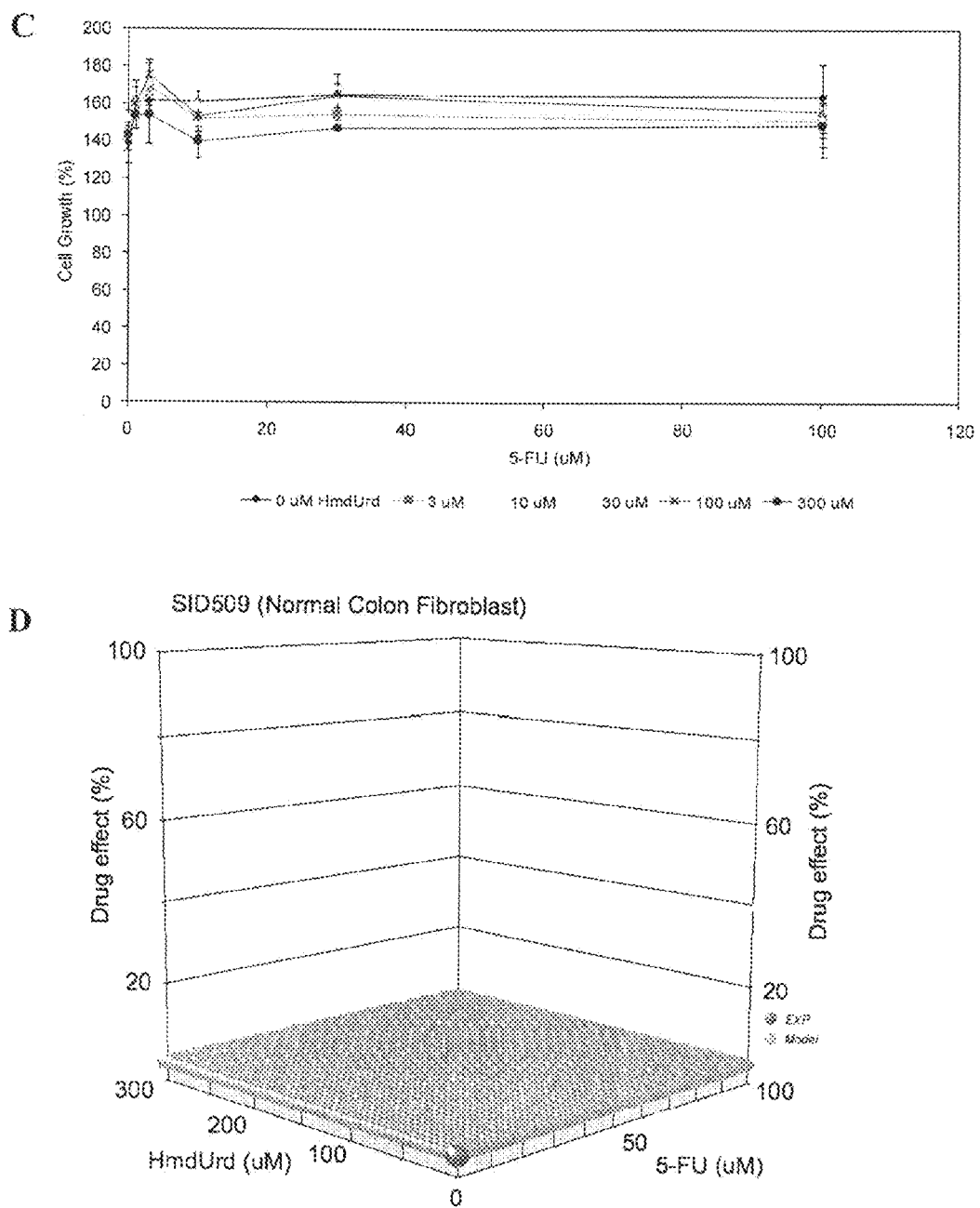
Figure 6A:
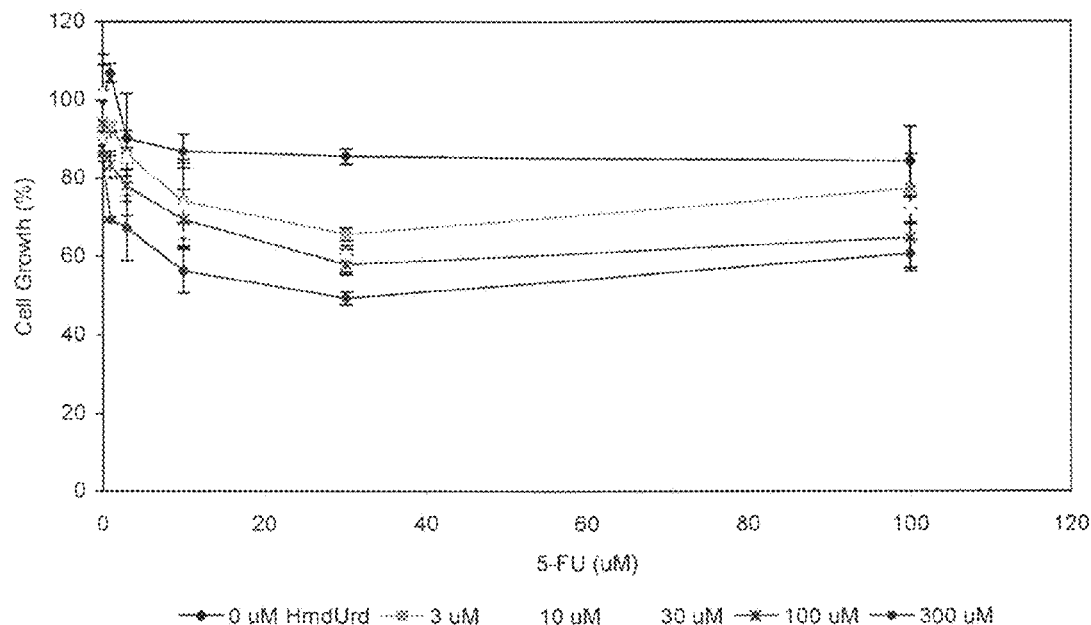
FIGS. 6A and 6B show the effect of combined 5-FU and HmdU treatment on cell growth of WI-38 and primary human fibroblasts, respectively.
Figure 6A:
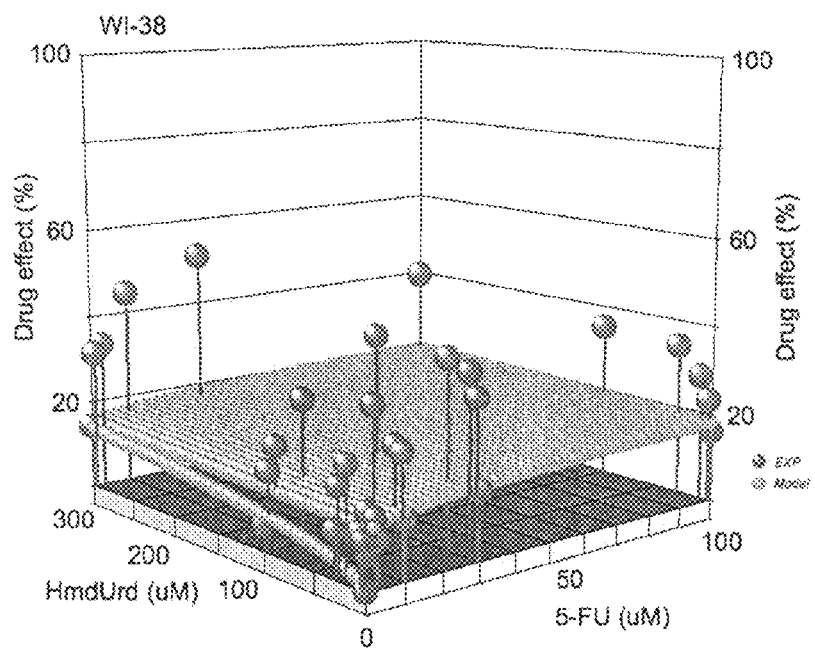
Figure 6B:
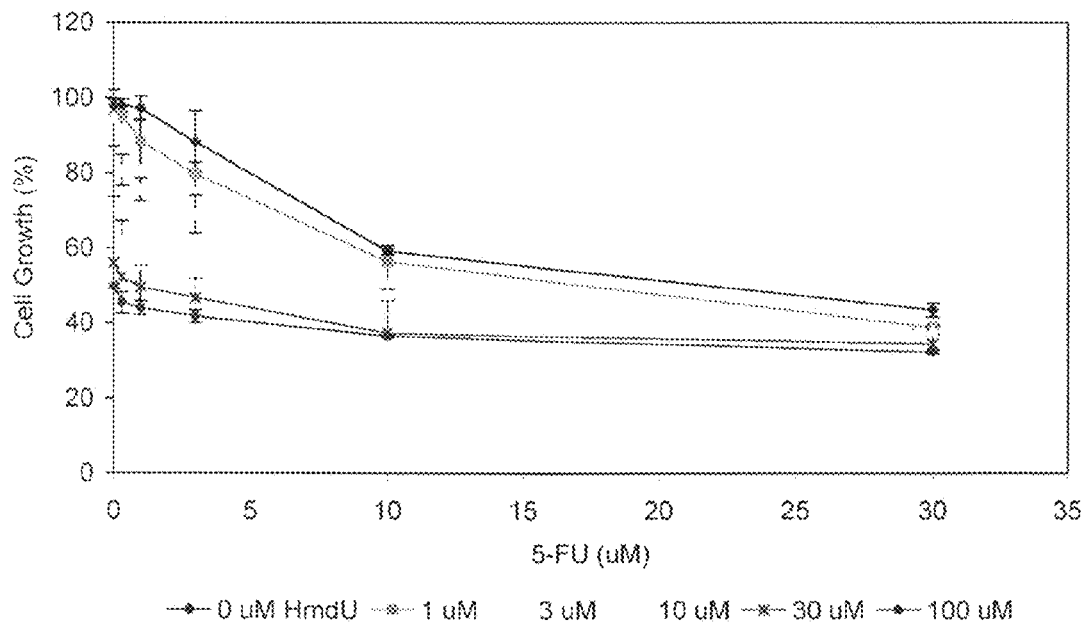
Figure 6B:
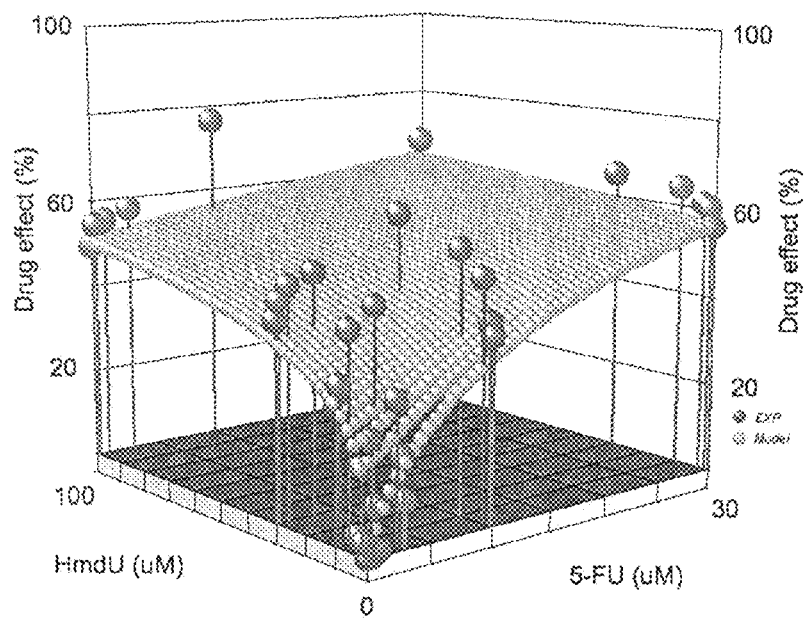
Figure 7:
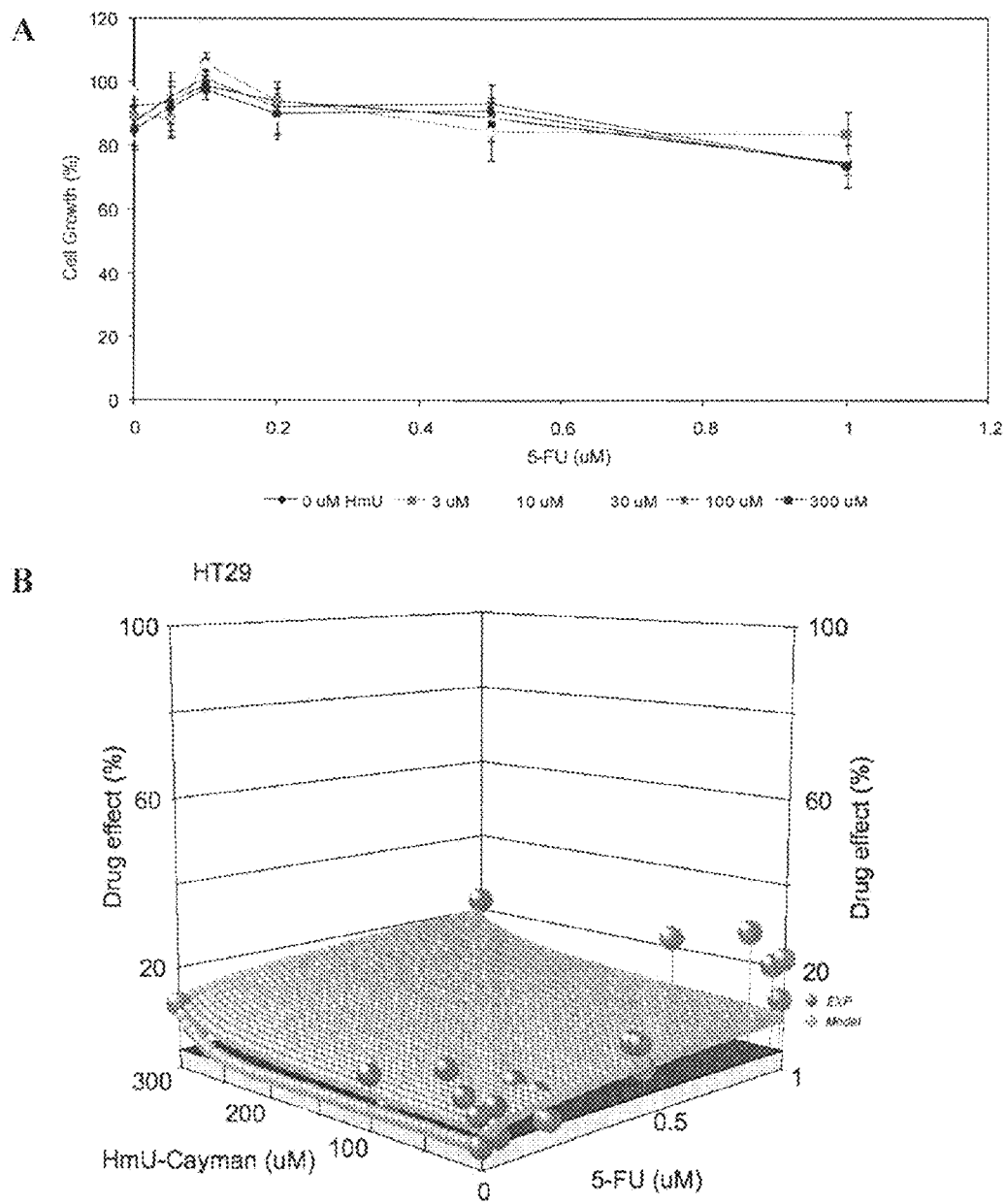
FIG. 7 shows the effect of combined 5-FU and HmU treatment on HT-29 cell growth.
Figure 7:
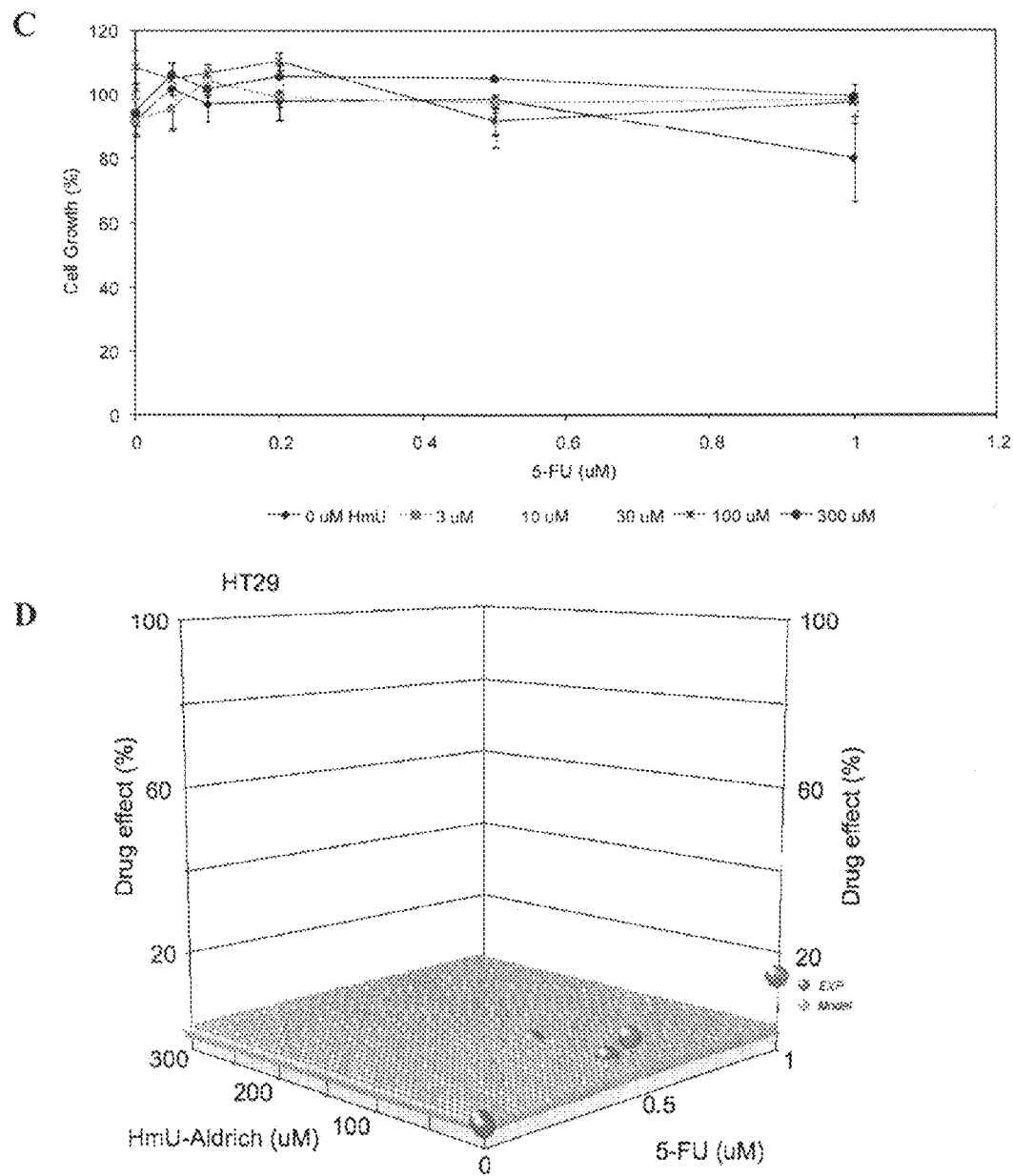

The HCT116 cell line is wild-type for p53, while the HT-29, panc-1 and EKVX cells have mutations in p53. The results in both wild-type and mutated p53 cells indicate that the synergistic effects of 5-FU and HmdU do not depend on the p53 pathway. In FIG. 4, the breast cancer cell line MDA-MB231 show more resistance to the combination of compounds than the cells in FIGS. 1-3. Additionally, normal colonic fibroblast cells, SID 507 and SID 509 (FIGS. 5A-5D) and normal lung cells, WI-38 (FIG. 6A) and primary human fibroblasts (FIG. 6B) are resistant to the combined treatment with the antineoplastic agents used.

Example II

Response of Colon Cancer Cells to 5-FU and HmdU Derivatives

Figure 8:
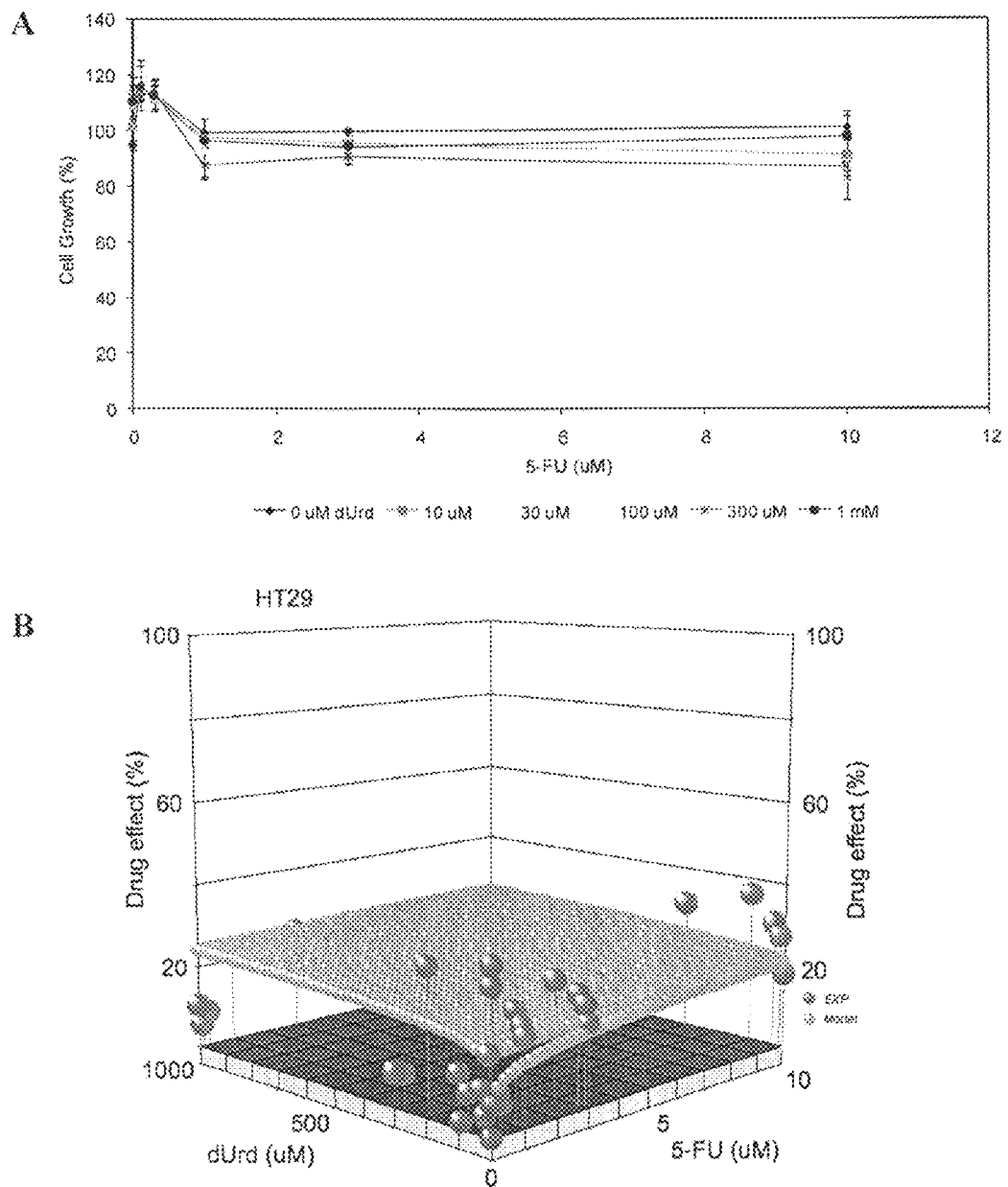
FIGS. 8A and B show the effect of combined 5-FU and dUrd treatment on HT-29 cell growth.
Figure 9:
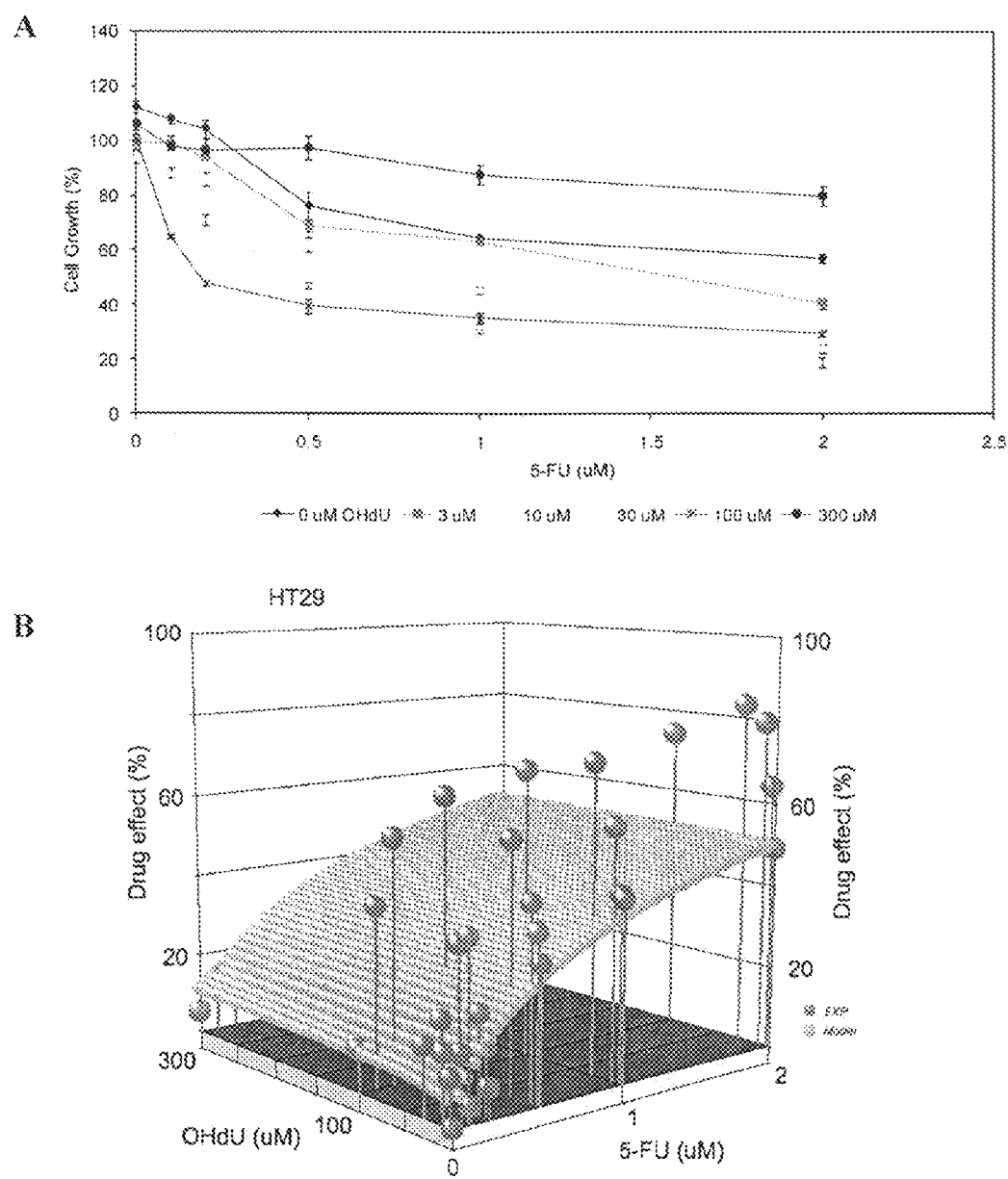
FIGS. 9A and B show the effect of combined 5-FU and OHdU treatment on HT-29 cell growth.

Further testing was performed on the HT-29 cell line to assess whether compounds that are structurally and/or functionally related to 5-FU and HmdU also display synergistic activity on growth inhibition. In a series of experiments 5-FU was tested with: (1) 5-Hydroxymethyluracil (HmU), a base form which is subsequently converted to a nucleoside form, HmdUrd; (2) Deoxyuridine (dUrd), a nucleoside which is different from HmdU by the lack of modification at the 5-carbon position; and (3) 5-Hydroxydeoxyuridine (OHdU), a nucleoside which is different from HmdU by the lack of a methyl group in the 5-carbon modification. These drugs, all related to HmdU, did not show any significant synergistic effects when combined with 5-FU. See FIG. 7A-7D (HmU—obtained from Cayman Chemical and Aldrich Chemical Company, respectively+5FU), FIG. 8A-8B (dUrd+5FU), and FIG. 9A-9B (OHdU+5FU).

Figure 10:
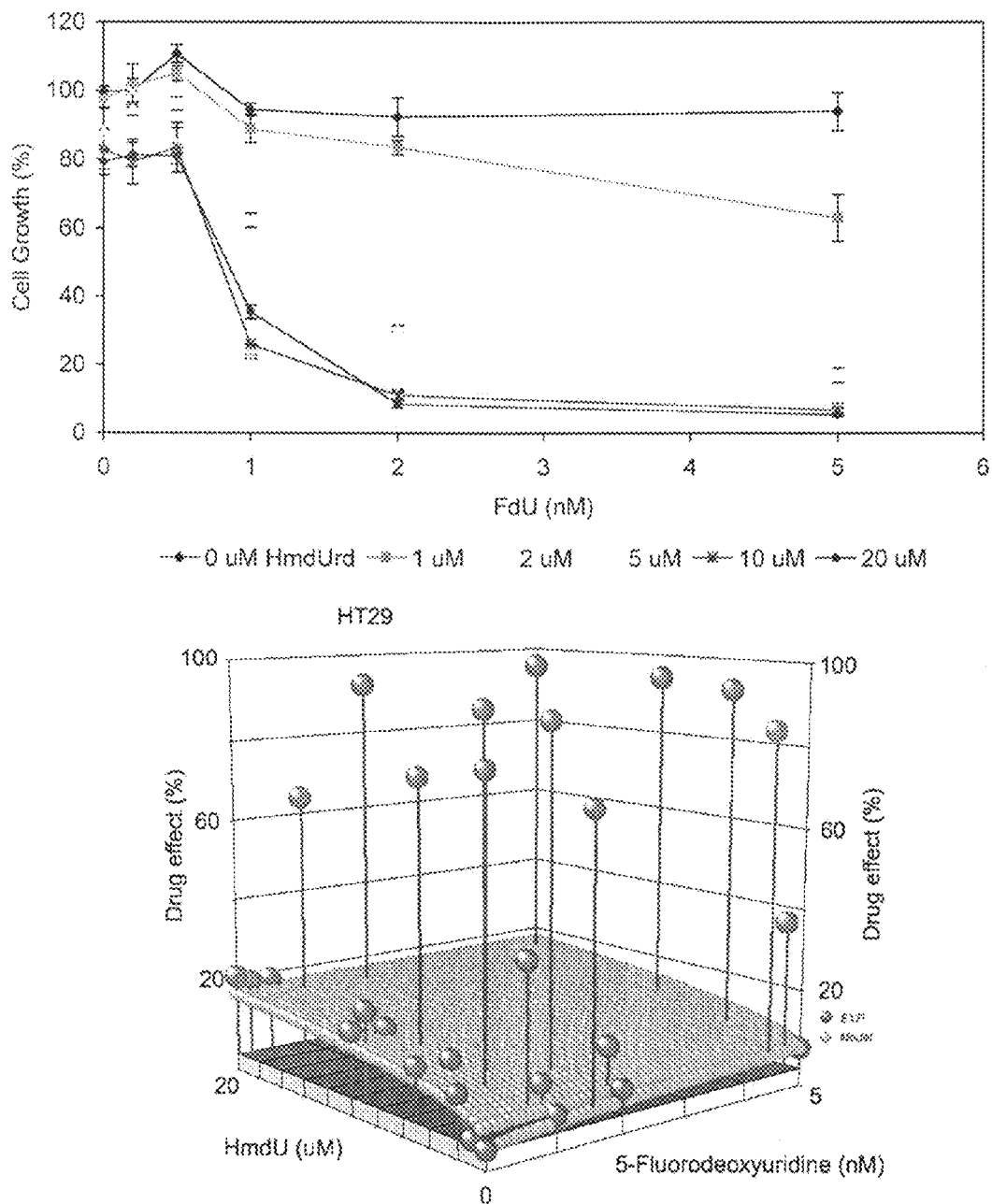
FIG. 10 shows the effect of combined 5-FdU and HmdU treatment on HT-29 cell growth.
Figure 11:
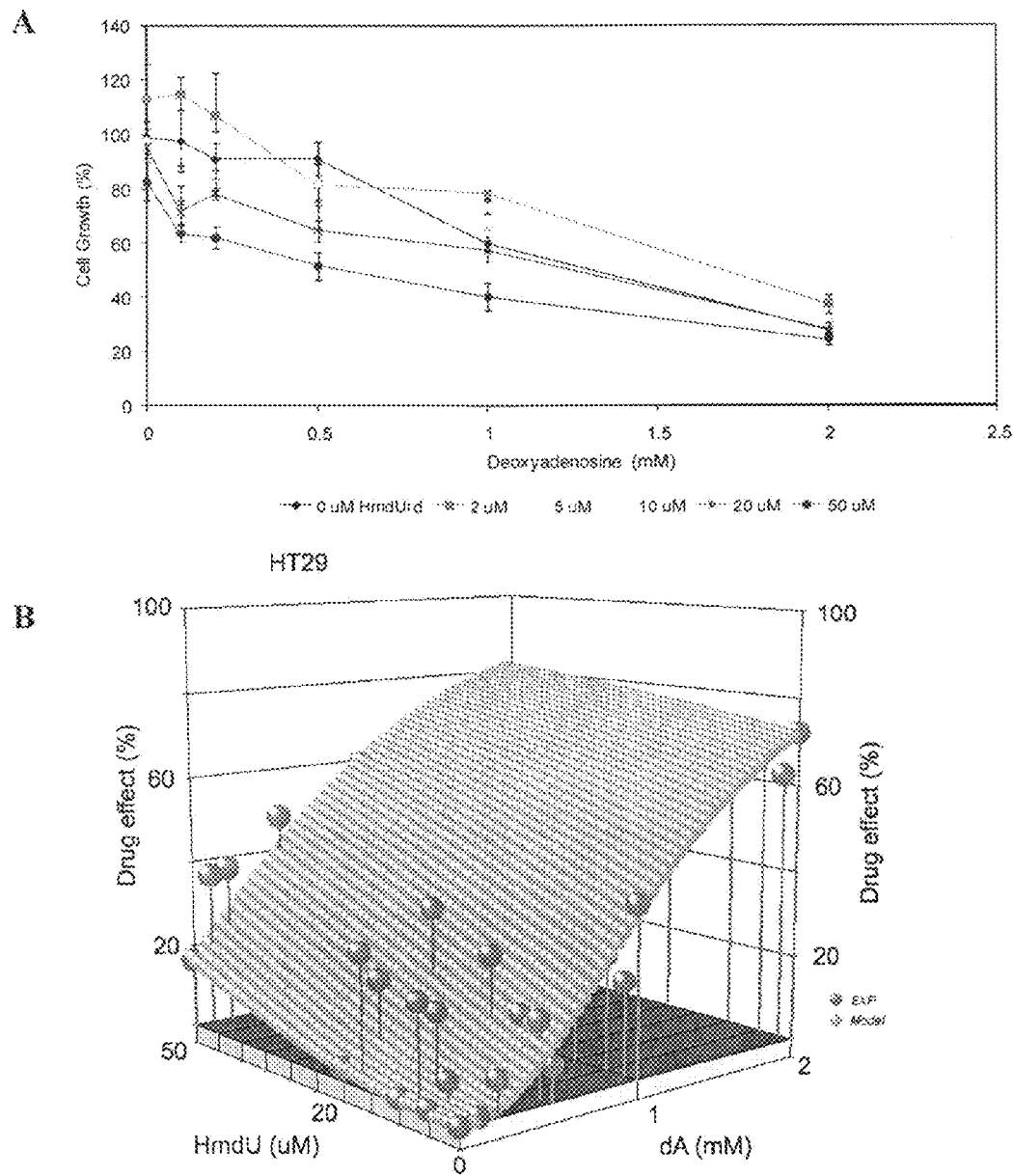
FIGS. 11A and B show the effect of combined deoxyadenosine and HmdU treatment on HT-29 cell growth.
Figure 12:
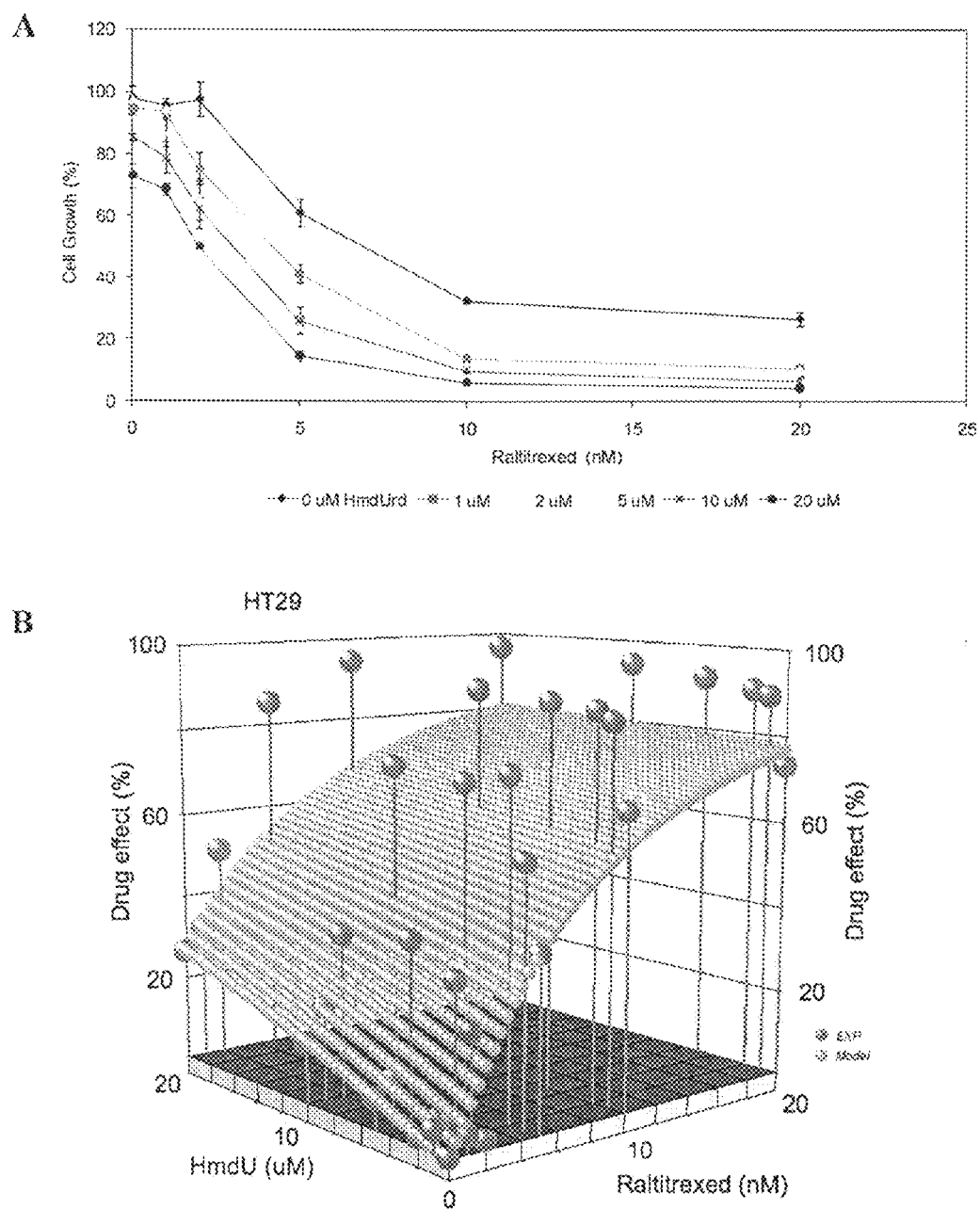
FIGS. 12A and B show the effect of combined Raltitrexed and HmdU treatment on HT-29 cell growth.

Another set of experiments tested several alternative 5-FU agents in combination with HmdU to determine if synergy exists when the agents were administered in combination. The 5-FU related compounds used with HmdU were: (1) 5-Fluorodeoxyuridine (5-FdU), a deoxyribonucleoside (2) Deoxyadenosine (dA), an agent capable of decreasing dTTP; and (3) Raltitrexed, a structural analog of 5,10-methylene tetrahydrofolate ($CH_2THF$), and a specific inhibitor of thymidylate synthase (TS). The results in FIG. 10 demonstrate that 5-FdU has strong synergy with HmdU. However, dA and Raltitrexed did not show any significant synergistic effects with HmdU. See FIGS. 11 (dA) and 12 (Raltitrexed). Thus, 5-FdU and 5-FU both demonstrate synergy when used against cancer cell lines in combination with HmdU.

Example III

Mechanism of Synergistic Effects of 5-FU and HmdU

Figure 13:
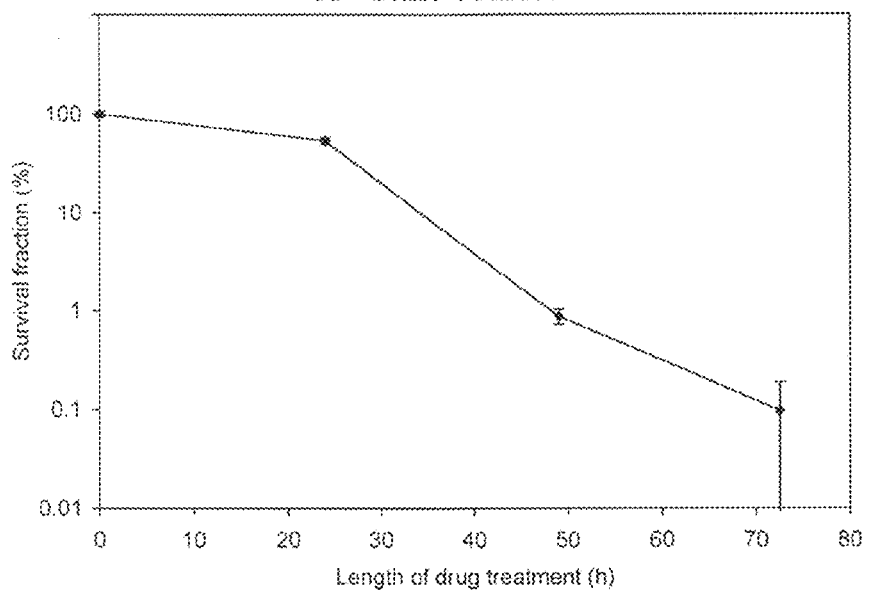
FIG. 13 is a clonogenic assay of HT-29 cells treated with 0.5 uM 5-FU and 5 uM HmdU over a 3 day period.
Figure 13:
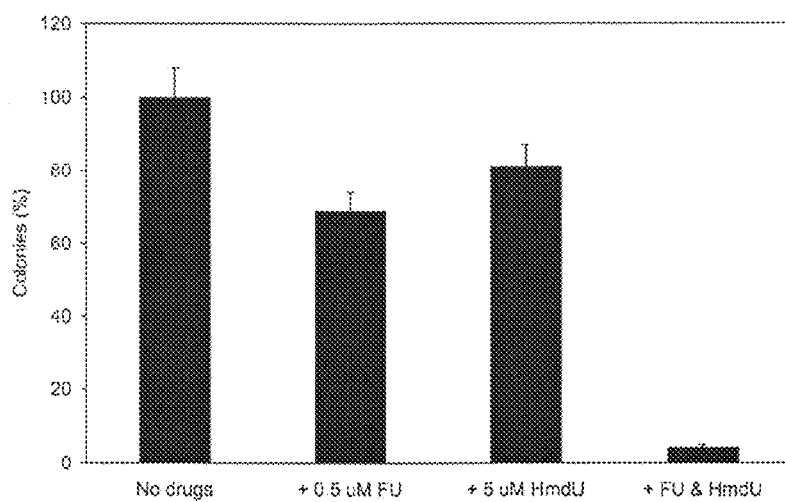
Figure 14:
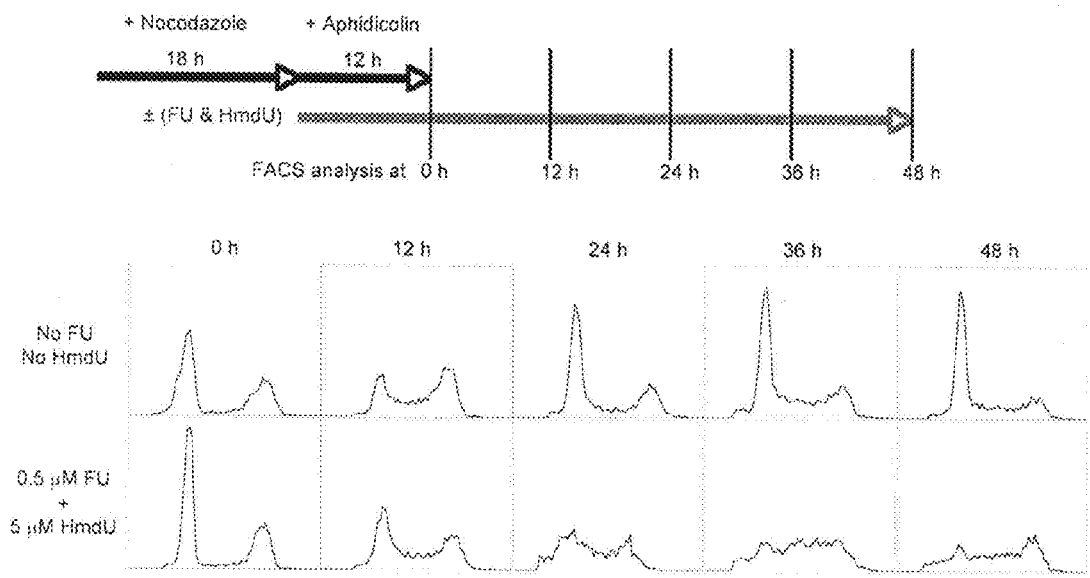
FIG. 14 shows a cell cycle analysis. Panel A is a cell cycle analysis of synchronized HT-29 cells with 5-FU, HmdU, and combined 5-FU/HmdU treatment over a period of two days. Panel B shows the effect of 3-aminobenzamide and caffeine on the cell cycle at 48 h of treatment with and without 5-FU and HmdU.
Figure 14:
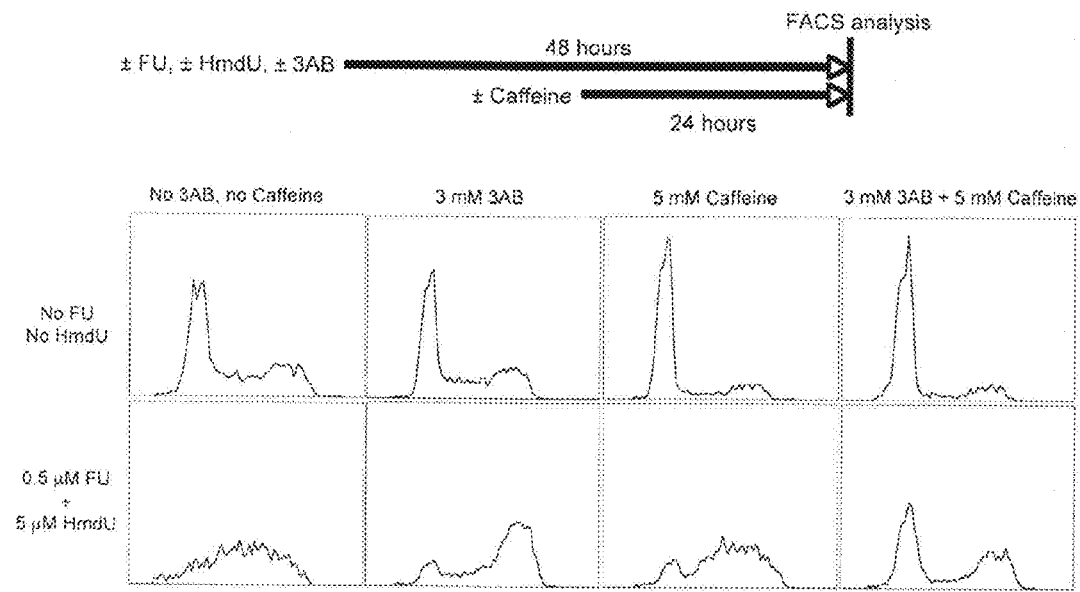

In this example, several additional experiments were performed to determine the mechanism underlying the synergistic effects seen with combined 5-FU and HmdU treatment. First, clonogenic assays were performed to determine the time course of the combination of 5-FU and HmdU. As shown in FIG. 13, the combined administration to HT-29 cells resulted not only in growth inhibition, but also in irreversible cell death. FIG. 13 also indicates that the complete effect of the treatment with the compounds required 48 hours. Subsequently, cell cycle distribution was assessed. FIG. 14A shows the cell cycle distribution of HT-29 cells synchronized with nocodazole and aphidicolin indicating that the cell cycle distribution of HT-29 cells synchronized with Nocodazole indicates that S phase cells are accumulated in 48 hours after treatment with 5-FU and HmdU. FIG. 14B shows that treatment with 3-aminobenzamide, a PARP-1 inhibitor, allows cells to complete DNA replication, and that additional caffeine treatment overcomes G2/M arrest.

Figure 15:
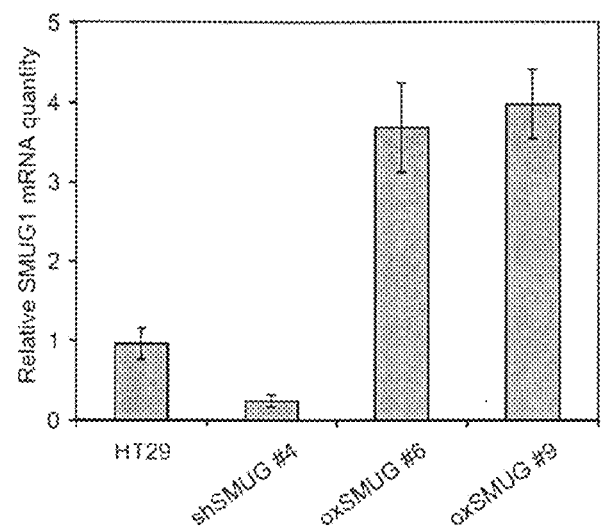
FIGS. 15A, B, C, D, E and F show the effect of SMUG1 expression on the synergistic effect of combined 5-FU and HmdU treatment in HT-29 cells.
Figure 15:
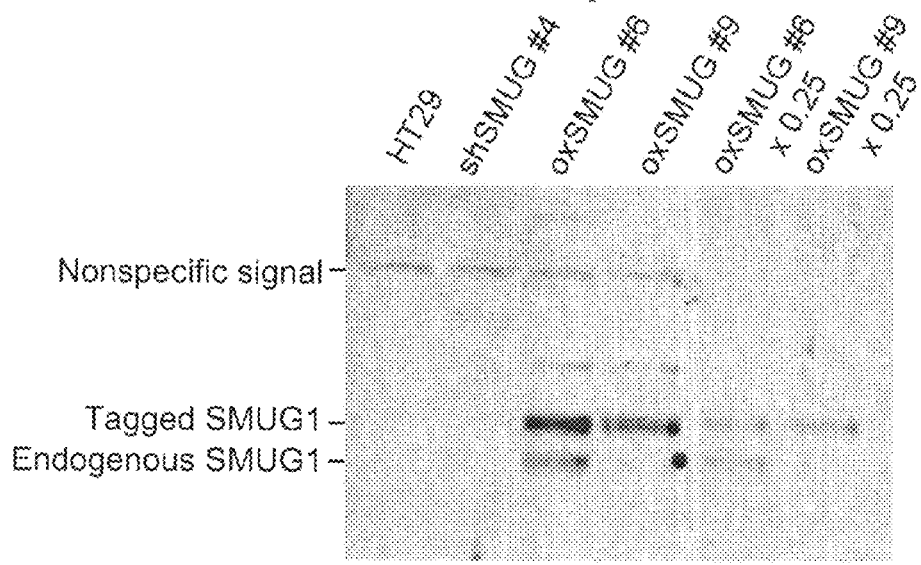
Figure 15:
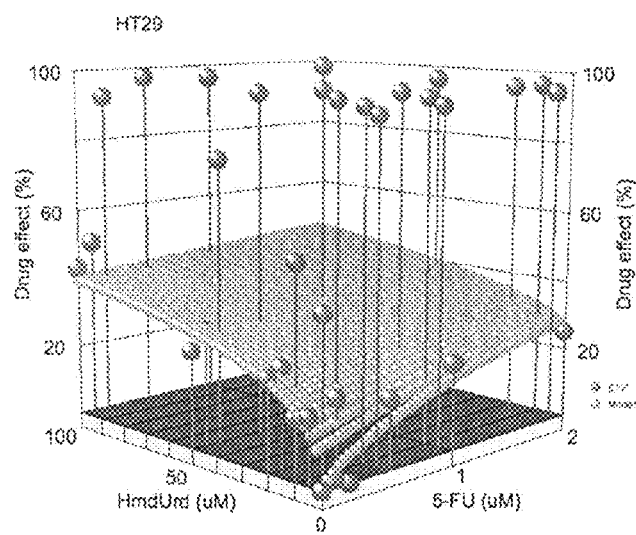
Figure 15:
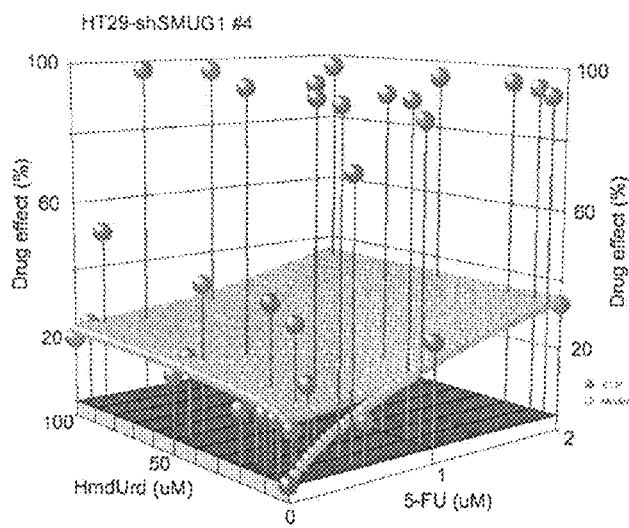
Figure 15:
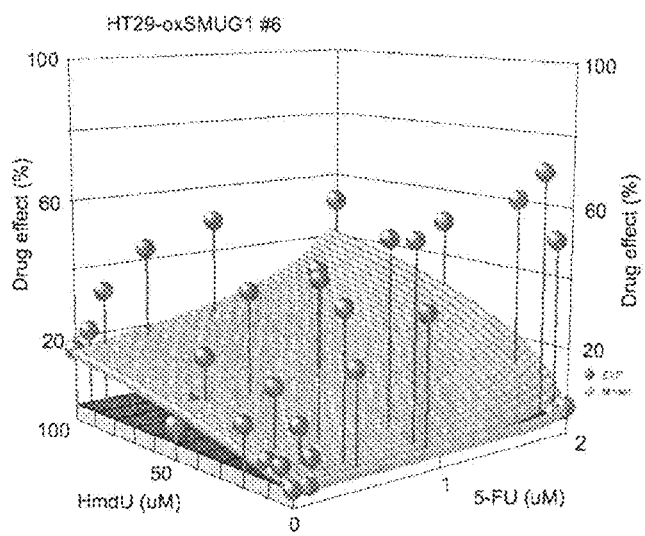
Figure 15:
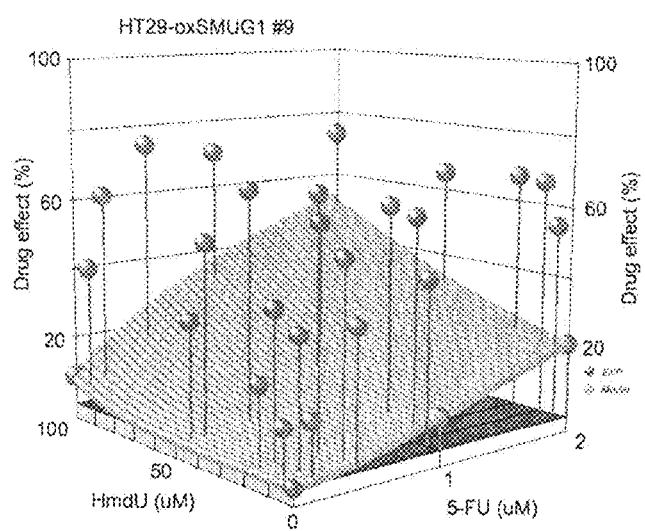

Other experiments investigated the effects of the SMUG1 protein on the combined 5-FU and HmdU treatment as shown in FIGS. 15A and 15B. By way of background, SMUG1 is a DNA glycosylase that removes HmdU from DNA. For these experiments, HT-29 cells were engineered in which cellular SMUG1 levels were either reduced or increased. FIG. 15 indicates that the SMUG1 decreased cells (shSMUG) showed a comparable sensitivity to the combined drug treatment, whereas the cells over expressing SMUG1 (oxSMUG) became more resistant to the same treatment. FIGS. 15C-15F show the results of the various SMUG1 expressing cells lines as interpreted with the CombiTool program. These results indicate that HmdU incorporation into DNA may be critical for the synergistic effects seen with the combination treatment.

Figure 16:
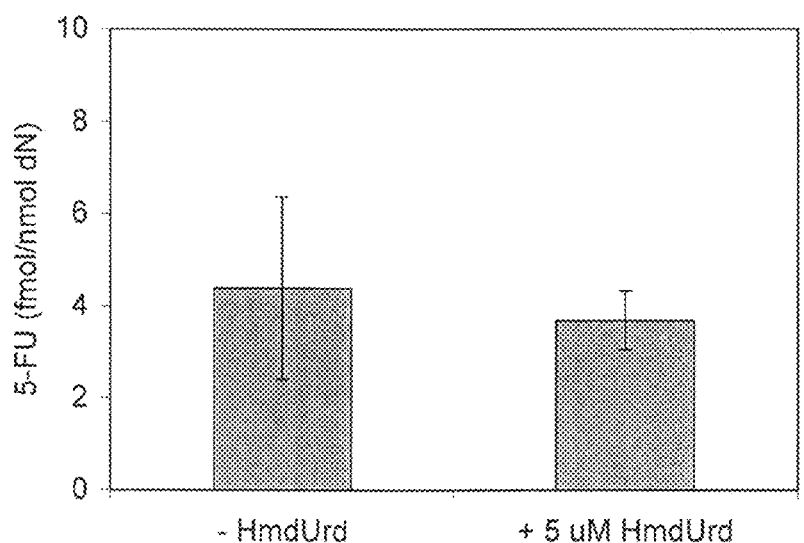
FIGS. 16A, B, C, and D show the incorporation of 5-FU and HmdU into DNA at 24 hours (FIG. 16 panels A and B), and RNA at 24 hours (FIG. 16 panels C and D).
Figure 16:
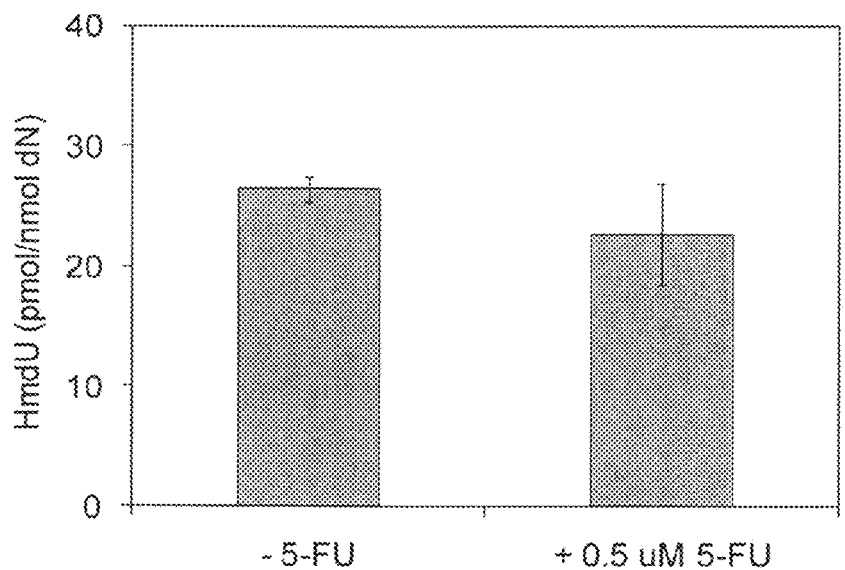
Figure 16:
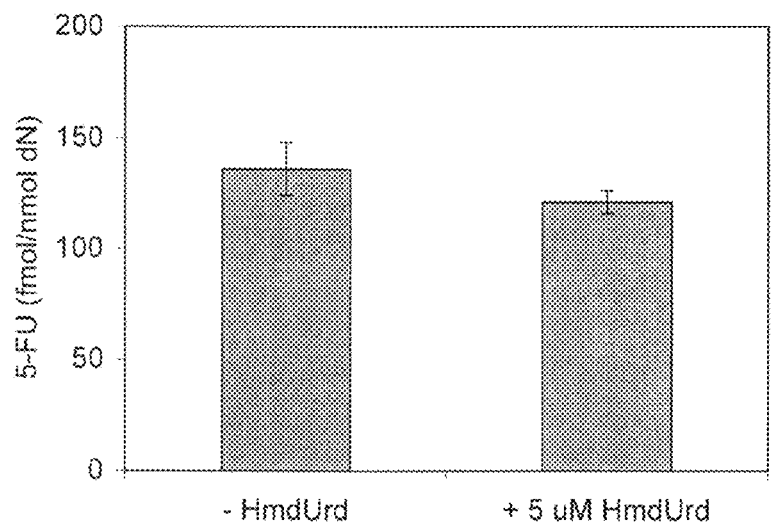
Figure 16:
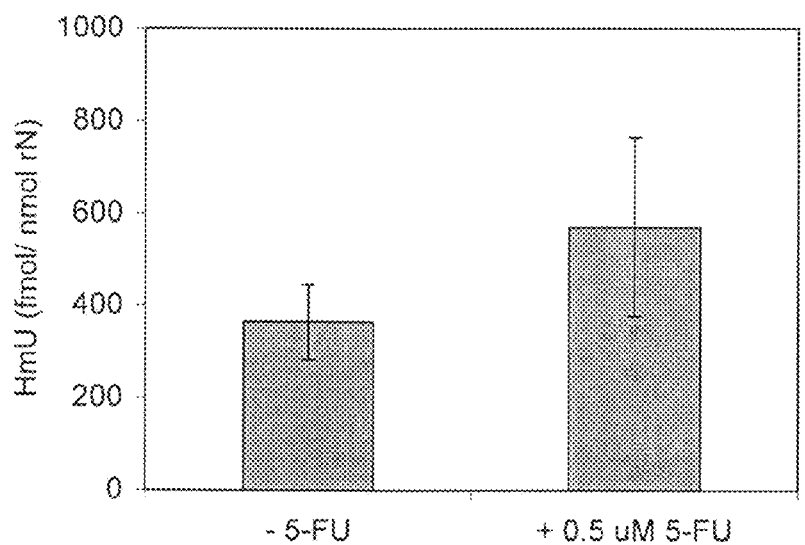
Figure 17:
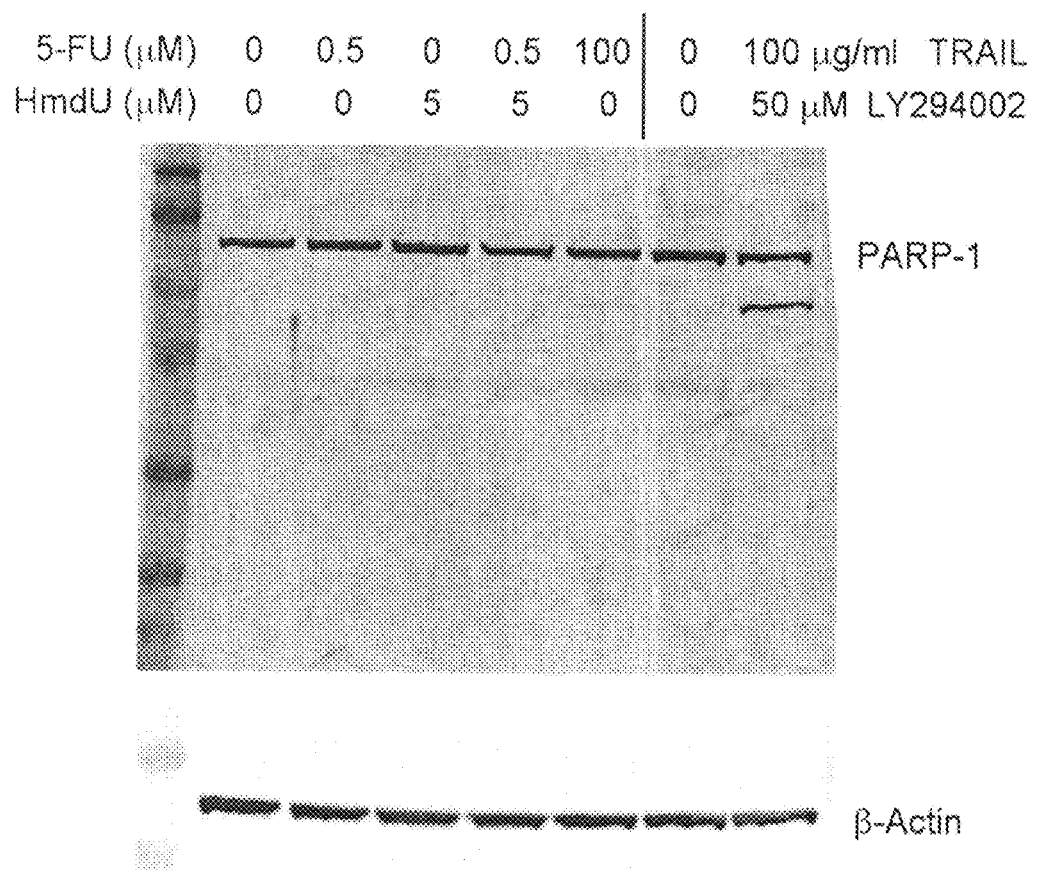
FIG. 17 demonstrates that treatment with 5-FU and HmdU does not induce PARP-1 cleavage in HT-29 cells.
Figure 18:
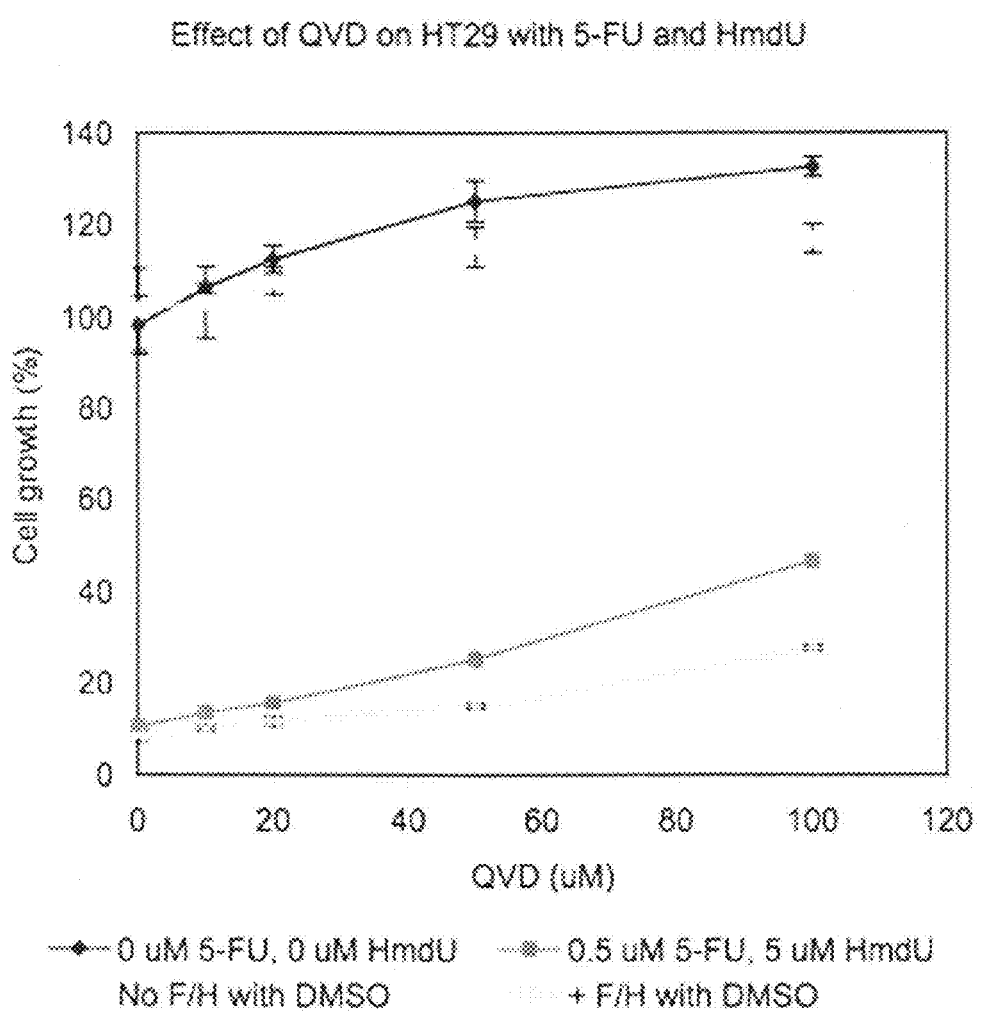
FIG. 18 shows the effect of QVD on HT-29 cells treated with a combination of 5-FU and HmdU.

Next, the level of incorporation of 5-FU and HmdU into DNA (FIG. 16A-B) and RNA (FIG. 16 C-D) was determined. Using tritium-labeled 5-FU and HmdU, measurements were taken to assess how much of the drugs were incorporated into cellular DNA and RNA during the treatment. The results indicate that the incorporation of 5-FU and HmdU into DNA or RNA was not increased in a synergistic manner. Likewise, the drug compounds' incorporation into DNA after 48 hours was not increased compared to those for 24 hours Further, experiments were performed to uncover whether the combined treatment with 5-FU and HmdU induces PARP1 cleavage, which would indicate that apoptosis is the pathway responsible for the cytotoxic effects. FIG. 17 shows that treatment of HT-29 with 5-FU and HmdU for 72 hours did not induce PARP cleavage (LY+TRAIL were used as a positive control). Likewise, FIG. 18 shows that QVD, a caspase inhibitor, did not rescue HT-29 from cell killing by the 5-FU and HmdU treatment. Both of the results in FIGS. 17 and 18 indicate that the cell killing by the combined drug treatment is not via apoptosis. However, the combination has a synergistic effect on the cytotoxicities of 5-FU and HmdU, and derivatives thereof.

Figure 19:
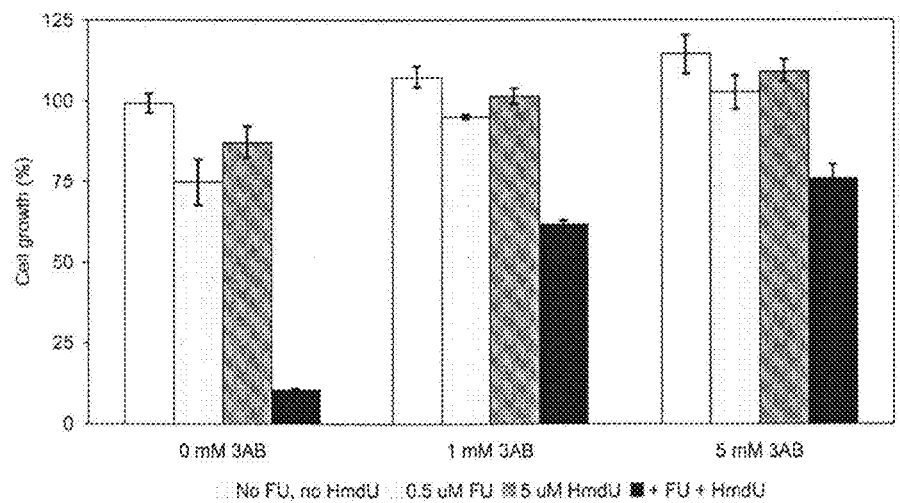
FIG. 19 shows the effect of PARP-1 inhibitors on cytotoxicity of 5-FU and HmdU.
Figure 19:
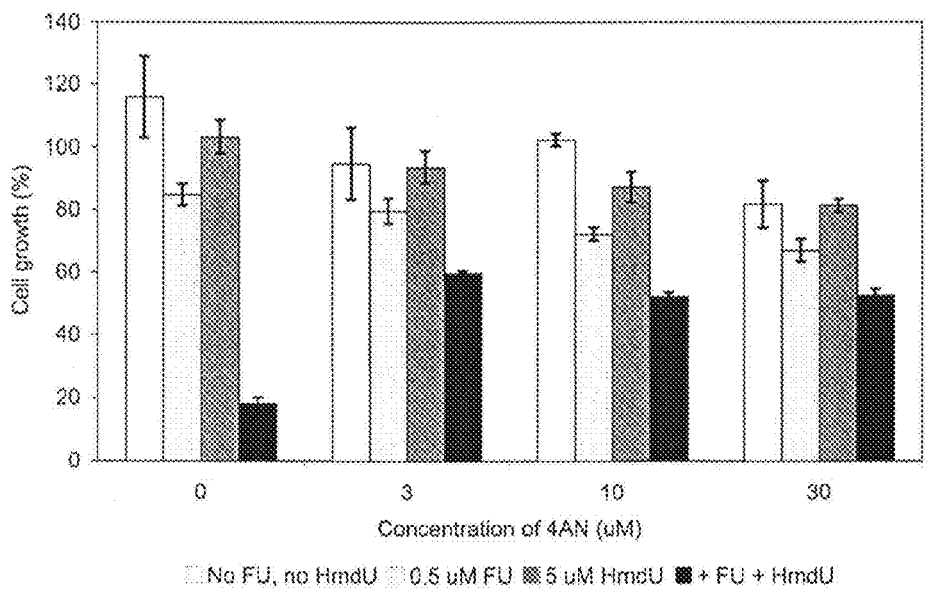

Taking account of effect of 3-aminobenzamide on cell cycle shown FIG. 14B, effects of PARP-1 inhibitors on cytotoxicity were examined. As a result, both 3-aminobenzamide and 4-amino-1,8-naphtalimide rescued cells from growth inhibition by 5-FU and HmdU (FIG. 19).

Figure 20:
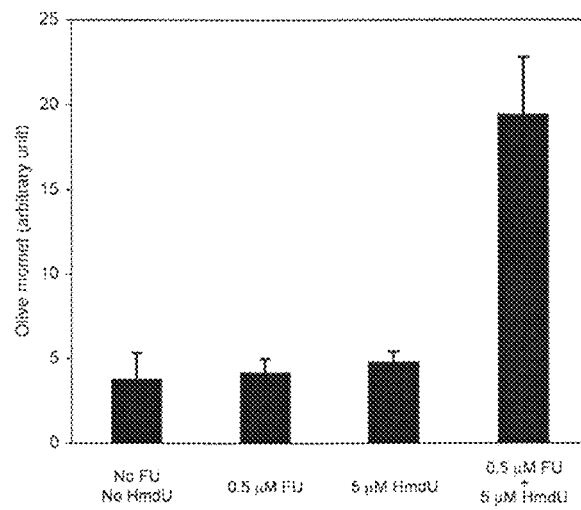
FIG. 20 shows the effects of 5-FU and HmdU on inducing single-strand breaks (and/or alkali labile sites) through 48 h of treatment.
Figure 20:
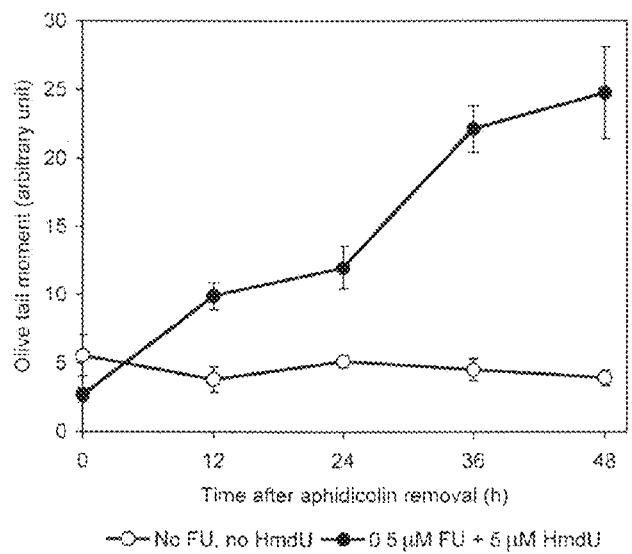

Since PARP-1 can be activated by DNA strand breaks, alkali comet assays were conducted to detect single-strand breaks (and/or alkali labile sites) in the cells treated with 5-FU and HmdU. As shown in FIG. 20, 5-FU and HmdU synergistically generate single-strand breaks (and/or alkali labile sites) through 48 h of treatment. These data strongly indicate that combinational treatment with 5-FU and HmdU introduces single-strand breaks and subsequently activate PARP-1, leading to cell death by necrosis through NAD depletion.

Example IV

In-Vivo Toxicity Studies of 5-FU and HmdU

The purpose of the study in this example was to determine the maximum tolerated dosage level of the HmdU and 5-FU mixture at a constant ratio of 20:1 (HmdU:5-FU), administered by intraperitoneal injection daily for five consecutive days to female out-bred nude mice. The mice were observed for two weeks following completion of dosing to monitor delayed toxicity and recovery.

Figure 21:
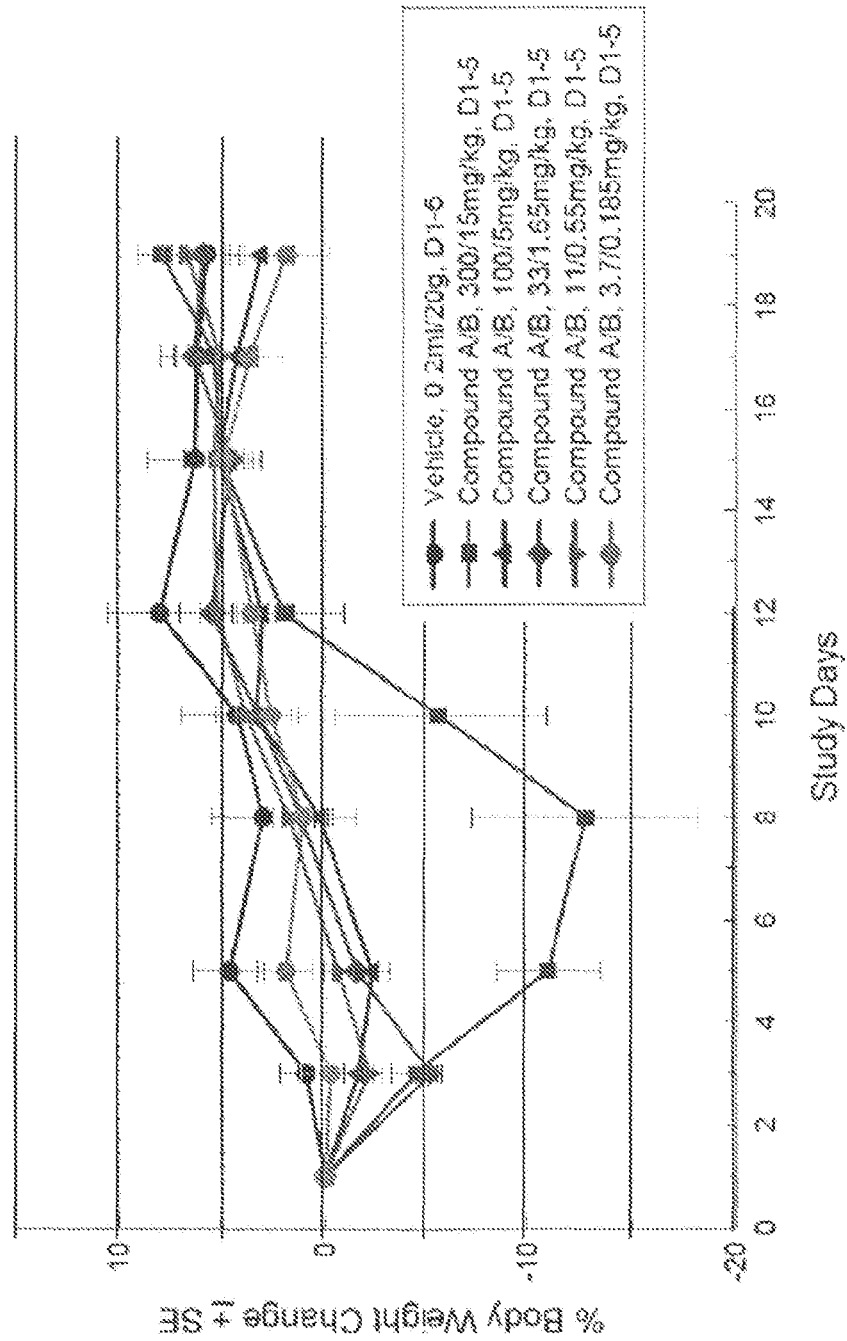
FIG. 21 shows the effect of 5-FU and HmdU on body weight of mice.

Treatment with the mixture of HmdU and 5-FU was tolerated at all dosage levels (300/15, 11/5, 33/1.65, 11/0.55, and 3.7/0.185 mg/kg), when administered by intraperitoneal injection daily for 5 days (i.e., days 1-5), resulting in no treatment-related mortality and minimal weight loss. The high dose combination group (300/15 mg/kg/inj) produced a weight loss of 12.7%, which was maximal on Day 8 and recovered by day 12. Weight loss for the remaining groups was ≤5%. with lost weight recovered in ~4 days. At study termination, necropsies revealed no remarkable findings. FIG. 21 shows body weight changes of mice injected with 5-FU and HmdU, indicating that the maximal tolerated dose level is at least 300 mg HmdU+15 mg 5-FU/kg/injection/day×5 days.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method of treating neoplasia in a patient in need thereof, said method comprising administering to said patient a therapeutically effective amount of:
   a) at least one compound selected from the group consisting of 5-Fluorouracil, 5-Fluorodeoxyuridine and capecitabine or other prodrug of 5-fluorouracil; and
   b) 5-hydroxymethyl-2'-deoxyuridine, or a prodrug thereof.

2. The method of claim 1, wherein said compounds of a) and b) are administered sequentially.

3. The method of claim 1, wherein said compounds of a) and b) are administered simultaneously.

4. The method of claim 1, wherein said neoplasia is a solid or liquid tumor.

5. The method of claim 4, wherein said solid tumor is selected from the group consisting of colon cancer, pancreatic cancer and lung cancer.

6. The method of claim 1, wherein said neoplasia is a refractory tumor.

7. The method of claim 1, further comprising an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes.

8. The method of claim 1, consisting of the administration of 5-Fluorouracil and 5-hydroxymethyl-2'-deoxyuridine.

9. The method of claim 1, consisting of the administration of 5-Fluorodeoxyuridine and 5-hydroxymethyl-2'-deoxyuridine.

10. A composition comprising:
    a) at least one of the compounds selected from the group consisting of 5-Fluorouracil, 5-Fluorodeoxyuridine and capecitabine or other prodrug of 5-fluorouracil; and
    b) 5-hydroxymethyl-2'-deoxyuridine or a prodrug thereof and a pharmaceutically acceptable carrier.

11. A composition comprising heterodinucleoside phosphates consisting of 5-Fluorodeoxyuridine and 5-hydroxymethyl-2'-deoxyuridine.

12. A kit for the treatment of neoplasia comprising the composition of claim 10.

13. The kit of claim 12, further comprising buffers, containers, and instructional materials.

\* \* \* \* \*